United States Patent
Ghosh

(10) Patent No.: US 10,532,213 B2
(45) Date of Patent: Jan. 14, 2020

(54) CRITERIA FOR DETERMINATION OF LOCAL TISSUE LATENCY NEAR PACING ELECTRODE

(71) Applicant: Medtronic, Inc., Minneapolis, MN (US)

(72) Inventor: Subham Ghosh, Blaine, MN (US)

(73) Assignee: Medtronic, Inc., Minneapolis, MN (US)

( * ) Notice: Subject to any disclaimer, the term of this patent is extended or adjusted under 35 U.S.C. 154(b) by 148 days.

(21) Appl. No.: 15/909,585

(22) Filed: Mar. 1, 2018

(65) Prior Publication Data

US 2018/0250514 A1 Sep. 6, 2018

Related U.S. Application Data

(60) Provisional application No. 62/466,627, filed on Mar. 3, 2017.

(51) Int. Cl.
*A61N 1/368* (2006.01)
*A61N 1/365* (2006.01)
(Continued)

(52) U.S. Cl.
CPC ......... *A61N 1/3682* (2013.01); *A61N 1/3684* (2013.01); *A61N 1/36514* (2013.01);
(Continued)

(58) Field of Classification Search
CPC .......... A61N 1/368; A61N 1/05; A61N 1/365; A61N 1/3684; A61N 1/3682;
(Continued)

(56) References Cited

U.S. PATENT DOCUMENTS 4,233,987 A 11/1980 Feingold
4,402,323 A 9/1983 White
(Continued)

FOREIGN PATENT DOCUMENTS

CN 1043621 A 7/1990
CN 1253761 A 5/2000
(Continued)

OTHER PUBLICATIONS

International Search Report and Written Opinion dated May 3, 2012 for International Application No. PCT/US2012/036262; 9 pages.
(Continued)

*Primary Examiner* — Carl H Layno
*Assistant Examiner* — Jon Eric C Morales

(57) ABSTRACT

A cardiac pacemaker is disclosed for pacing cardiac tissue to improve synchrony between the atria and ventricles and/or between the left and right ventricles. A pulse generator is configured to deliver a pacing pulse to a patient's ventricle at an atrioventricular (AV) delay following a preceding atrial event. A sensing circuitry configured to sense a signal from the patient's ventricle following delivery of a said pacing pulse. A processing circuitry coupled to the pulse generator and the sensing circuitry and configured to control the pulse generator, the processing circuitry further configured to: (1) acquire from the sensed signal a set of features; (2) determine whether the ventricular pacing pulse effectively captures the patient's ventricle using the set of features; (3) determine whether one or more tissue latency conditions are present. The one or more pacing pulse parameters are adjusted, in response to determining that tissue latency is present.

21 Claims, 10 Drawing Sheets

(51) Int. Cl.
*A61N 1/37* (2006.01)
*A61B 5/0464* (2006.01)
*A61B 5/0452* (2006.01)
*A61B 5/0472* (2006.01)
*A61N 1/05* (2006.01)
*A61B 5/042* (2006.01)

(52) U.S. Cl.
CPC ....... *A61N 1/36592* (2013.01); *A61N 1/3706* (2013.01); *A61B 5/0422* (2013.01); *A61B 5/0464* (2013.01); *A61B 5/0472* (2013.01); *A61B 5/04525* (2013.01); *A61N 1/056* (2013.01)

(58) Field of Classification Search
CPC ................ A61N 1/3651; A61B 5/0452; A61B 5/04085; A61B 5/0464
See application file for complete search history.

(56) References Cited

U.S. PATENT DOCUMENTS

| | | | |
|---|---|---|---|
| 4,428,378 A | 1/1984 | Anderson |
| 4,497,326 A | 2/1985 | Curry |
| 4,566,456 A | 1/1986 | Koning et al. |
| 4,593,702 A | 6/1986 | Kepski |
| 4,674,511 A | 6/1987 | Cartmell |
| 4,763,660 A | 8/1988 | Kroll et al. |
| 4,777,955 A | 10/1988 | Brayten et al. |
| 4,787,389 A | 11/1988 | Tarjan |
| 4,979,507 A | 12/1990 | Heinz et al. |
| 5,052,388 A | 10/1991 | Sivula |
| 5,054,496 A | 10/1991 | Wen et al. |
| 5,311,873 A | 5/1994 | Savard et al. |
| 5,331,960 A | 7/1994 | Lavine |
| 5,334,220 A | 8/1994 | Sholder |
| 5,443,492 A | 8/1995 | Stokes et al. |
| 5,485,849 A | 1/1996 | Panescu et al. |
| 5,514,163 A | 5/1996 | Markowitz et al. |
| 5,552,645 A | 9/1996 | Weng |
| 5,628,778 A | 5/1997 | Kruse et al. |
| 5,671,752 A | 9/1997 | Sinderby et al. |
| 5,683,429 A | 11/1997 | Mehra |
| 5,683,432 A | 11/1997 | Goedeke |
| 5,687,737 A | 11/1997 | Branham et al. |
| 5,810,740 A | 9/1998 | Paisner |
| 5,876,336 A | 3/1999 | Swanson et al. |
| 5,891,045 A | 4/1999 | Albrecht et al. |
| 5,922,014 A | 7/1999 | Warman et al. |
| 6,055,448 A | 4/2000 | Anderson et al. |
| 6,128,535 A | 10/2000 | Maarse et al. |
| 6,141,588 A | 10/2000 | Cox et al. |
| 6,187,032 B1 | 2/2001 | Ohyu et al. |
| 6,205,357 B1 | 3/2001 | Ideker et al. |
| 6,226,542 B1 | 5/2001 | Reisfeld |
| 6,236,883 B1 | 5/2001 | Ciaccio et al. |
| 6,243,603 B1 | 6/2001 | Ideker et al. |
| 6,246,898 B1 | 6/2001 | Vesely et al. |
| 6,301,496 B1 | 10/2001 | Reisfeld |
| 6,311,089 B1 | 10/2001 | Mann et al. |
| 6,330,476 B1 | 12/2001 | Ben-Haim et al. |
| 6,358,214 B1 | 3/2002 | Tereschouk |
| 6,377,856 B1 | 4/2002 | Carson |
| 6,381,493 B1 | 4/2002 | Stadler et al. |
| 6,393,316 B1 | 5/2002 | Gillberg et al. |
| 6,418,346 B1 | 7/2002 | Nelson |
| 6,442,433 B1 | 8/2002 | Linberg |
| 6,456,867 B2 | 9/2002 | Reisfeld |
| 6,473,638 B2 | 10/2002 | Ferek-Petric |
| 6,480,745 B2 | 11/2002 | Nelson |
| 6,484,118 B1 | 11/2002 | Govari |
| 6,507,756 B1 | 1/2003 | Heynen et al. |
| 6,532,379 B2 | 3/2003 | Stratbucker |
| 6,584,343 B1 | 6/2003 | Ransbury et al. |
| 6,599,250 B2 | 7/2003 | Webb |
| 6,625,482 B1 | 9/2003 | Panescu et al. |
| 6,640,136 B1 | 10/2003 | Helland et al. |
| 6,650,927 B1 | 11/2003 | Keidar |
| 6,766,189 B2 | 7/2004 | Yu et al. |
| 6,772,004 B2 | 8/2004 | Rudy |
| 6,804,555 B2 | 10/2004 | Warkentin |
| 6,847,836 B1 | 1/2005 | Sujdak |
| 6,856,830 B2 | 2/2005 | He |
| 6,882,882 B2 | 4/2005 | Struble et al. |
| 6,885,889 B2 | 4/2005 | Chinchoy |
| 6,915,149 B2 | 7/2005 | Ben-Haim |
| 6,968,237 B2 | 11/2005 | Doan et al. |
| 6,975,900 B2 | 12/2005 | Rudy et al. |
| 6,978,184 B1 | 12/2005 | Marcus et al. |
| 6,980,675 B2 | 12/2005 | Evron et al. |
| 7,016,719 B2 | 3/2006 | Rudy et al. |
| 7,031,777 B2 | 4/2006 | Hine et al. |
| 7,058,443 B2 | 6/2006 | Struble |
| 7,062,315 B2 | 6/2006 | Koyrakh et al. |
| 7,092,759 B2 | 8/2006 | Nehls et al. |
| 7,142,922 B2 | 11/2006 | Spinelli et al. |
| 7,184,835 B2 | 2/2007 | Kramer et al. |
| 7,215,998 B2 | 5/2007 | Wesselink et al. |
| 7,238,158 B2 | 7/2007 | Abend |
| 7,286,866 B2 | 10/2007 | Okerlund et al. |
| 7,308,297 B2 | 12/2007 | Reddy et al. |
| 7,308,299 B2 | 12/2007 | Burrell et al. |
| 7,313,444 B2 | 12/2007 | Pianca et al. |
| 7,321,677 B2 | 1/2008 | Evron et al. |
| 7,346,381 B2 | 3/2008 | Okerlund et al. |
| 7,398,116 B2 | 7/2008 | Edwards |
| 7,426,412 B1 | 9/2008 | Schecter |
| 7,454,248 B2 | 11/2008 | Burrell et al. |
| 7,499,743 B2 | 3/2009 | Vass et al. |
| 7,509,170 B2 | 3/2009 | Zhang et al. |
| 7,565,190 B2 | 7/2009 | Okerlund et al. |
| 7,587,074 B2 | 9/2009 | Zarkh et al. |
| 7,599,730 B2 | 10/2009 | Hunter et al. |
| 7,610,088 B2 | 10/2009 | Chinchoy |
| 7,613,500 B2 | 11/2009 | Vass et al. |
| 7,616,993 B2 | 11/2009 | Müssig et al. |
| 7,664,550 B2 | 2/2010 | Eick et al. |
| 7,684,863 B2 | 3/2010 | Parikh et al. |
| 7,742,629 B2 | 6/2010 | Zarkh et al. |
| 7,747,047 B2 | 6/2010 | Okerlund et al. |
| 7,751,882 B1 | 7/2010 | Helland et al. |
| 7,769,451 B2 | 8/2010 | Yang et al. |
| 7,778,685 B2 | 8/2010 | Evron et al. |
| 7,778,686 B2 | 8/2010 | Vass et al. |
| 7,787,951 B1 | 8/2010 | Min |
| 7,813,785 B2 | 10/2010 | Okerlund et al. |
| 7,818,040 B2 | 10/2010 | Spear et al. |
| 7,848,807 B2 | 12/2010 | Wang |
| 7,860,580 B2 | 12/2010 | Falk et al. |
| 7,894,889 B2 | 2/2011 | Zhang |
| 7,912,544 B1 | 3/2011 | Min et al. |
| 7,917,214 B1 | 3/2011 | Gill et al. |
| 7,941,213 B2 | 5/2011 | Markowitz et al. |
| 7,953,475 B2 | 5/2011 | Harlev et al. |
| 7,953,482 B2 | 5/2011 | Hess |
| 7,983,743 B2 | 7/2011 | Rudy et al. |
| 7,996,063 B2 | 8/2011 | Vass et al. |
| 7,996,070 B2 | 8/2011 | van Dam et al. |
| 8,010,194 B2 | 8/2011 | Muller |
| 8,019,402 B1 | 9/2011 | Kryzpow et al. |
| 8,019,409 B2 | 9/2011 | Rosenberg et al. |
| 8,032,229 B2 | 10/2011 | Gerber et al. |
| 8,036,743 B2 | 10/2011 | Savage et al. |
| 8,060,185 B2 | 11/2011 | Hunter et al. |
| 8,150,513 B2 | 4/2012 | Chinchoy |
| 8,160,700 B1 | 4/2012 | Ryu et al. |
| 8,175,703 B2 | 5/2012 | Dong et al. |
| 8,180,428 B2 | 5/2012 | Kaiser et al. |
| 8,195,292 B2 | 6/2012 | Rosenberg et al. |
| 8,213,693 B1 | 7/2012 | Li |
| 8,214,041 B2 | 7/2012 | Van Gelder et al. |
| 8,265,738 B1 | 9/2012 | Min et al. |
| 8,285,377 B2 | 10/2012 | Rosenberg et al. |
| 8,295,943 B2 | 10/2012 | Eggen et al. |

(56) References Cited

U.S. PATENT DOCUMENTS

| | | |
|---|---|---|
| 8,326,419 B2 | 12/2012 | Rosenberg et al. |
| 8,332,030 B2 | 12/2012 | Hess et al. |
| 8,380,308 B2 | 2/2013 | Rosenberg et al. |
| 8,401,616 B2 | 3/2013 | Verard et al. |
| 8,478,388 B2 | 7/2013 | Nguyen et al. |
| 8,509,896 B2 | 8/2013 | Doerr et al. |
| 8,527,051 B1 | 9/2013 | Hedberg et al. |
| 8,583,230 B2 | 11/2013 | Ryu et al. |
| 8,615,298 B2 | 12/2013 | Ghosh et al. |
| 8,617,082 B2 | 12/2013 | Zhang et al. |
| 8,620,433 B2 | 12/2013 | Ghosh et al. |
| 8,639,333 B2 | 1/2014 | Stadler et al. |
| 8,694,099 B2 | 4/2014 | Ghosh et al. |
| 8,731,642 B2 | 5/2014 | Zarkh et al. |
| 8,738,132 B1 | 5/2014 | Ghosh et al. |
| 8,738,813 B1 | 5/2014 | Natanzon |
| 8,744,576 B2 | 6/2014 | Munsterman et al. |
| 8,750,998 B1 | 6/2014 | Ghosh |
| 8,768,465 B2 | 7/2014 | Ghosh et al. |
| 8,805,504 B2 | 8/2014 | Sweeney |
| 8,861,830 B2 | 10/2014 | Brada et al. |
| 8,972,228 B2 | 3/2015 | Ghosh et al. |
| 9,002,454 B2 | 4/2015 | Ghosh et al. |
| 9,037,238 B2 | 5/2015 | Stadler et al. |
| 9,155,897 B2 | 10/2015 | Ghosh et al. |
| 9,199,087 B2 | 12/2015 | Stadler et al. |
| 9,265,951 B2 | 2/2016 | Sweeney |
| 9,265,954 B2 | 2/2016 | Ghosh |
| 9,265,955 B2 | 2/2016 | Ghosh |
| 9,278,219 B2 | 3/2016 | Ghosh |
| 9,278,220 B2 | 3/2016 | Ghosh |
| 9,282,907 B2 | 3/2016 | Ghosh |
| 9,320,446 B2 | 4/2016 | Gillberg et al. |
| 9,474,457 B2 | 10/2016 | Ghosh et al. |
| 9,486,151 B2 | 11/2016 | Ghosh et al. |
| 9,510,763 B2 | 12/2016 | Gosh et al. |
| 9,586,050 B2 | 3/2017 | Ghosh et al. |
| 9,586,052 B2 | 3/2017 | Gillberg et al. |
| 9,591,982 B2 | 3/2017 | Ghosh et al. |
| 9,764,143 B2 | 9/2017 | Ghosh et al. |
| 9,768,319 B2 | 9/2017 | Kamata |
| 9,776,009 B2 | 10/2017 | Ghosh et al. |
| 9,789,319 B2 | 10/2017 | Sambelashvili |
| 9,924,884 B2 | 3/2018 | Ghosh et al. |
| 2002/0072682 A1 | 6/2002 | Hopman et al. |
| 2002/0087089 A1 | 7/2002 | Ben-Haim |
| 2002/0143264 A1 | 10/2002 | Ding et al. |
| 2002/0161307 A1 | 10/2002 | Yu et al. |
| 2002/0169484 A1 | 11/2002 | Mathis et al. |
| 2003/0018277 A1 | 1/2003 | He |
| 2003/0050670 A1 | 3/2003 | Spinelli et al. |
| 2003/0105495 A1 | 6/2003 | Yu et al. |
| 2003/0236466 A1 | 12/2003 | Tarjan et al. |
| 2004/0015081 A1 | 1/2004 | Kramer et al. |
| 2004/0059237 A1 | 3/2004 | Narayan et al. |
| 2004/0097806 A1 | 5/2004 | Hunter et al. |
| 2004/0102812 A1 | 5/2004 | Yonce et al. |
| 2004/0122479 A1 | 6/2004 | Spinelli et al. |
| 2004/0162496 A1 | 8/2004 | Yu et al. |
| 2004/0172078 A1 | 9/2004 | Chinchoy |
| 2004/0172079 A1 | 9/2004 | Chinchoy |
| 2004/0193223 A1 | 9/2004 | Kramer et al. |
| 2004/0215245 A1 | 10/2004 | Stahmann et al. |
| 2004/0215252 A1 | 10/2004 | Verbeek et al. |
| 2004/0220635 A1 | 11/2004 | Burnes |
| 2004/0267321 A1 | 12/2004 | Boileau et al. |
| 2005/0008210 A1 | 1/2005 | Evron et al. |
| 2005/0027320 A1 | 2/2005 | Nehls et al. |
| 2005/0090870 A1 | 4/2005 | Hine et al. |
| 2005/0096522 A1 | 5/2005 | Reddy et al. |
| 2005/0107839 A1 | 5/2005 | Sanders |
| 2005/0149138 A1 | 7/2005 | Min et al. |
| 2006/0074285 A1 | 4/2006 | Zarkh et al. |
| 2006/0224198 A1 | 10/2006 | Dong et al. |
| 2006/0235478 A1 | 10/2006 | Van Gelder et al. |
| 2006/0253162 A1 | 11/2006 | Zhang et al. |
| 2007/0142871 A1 | 6/2007 | Libbus et al. |
| 2007/0167809 A1 | 7/2007 | Dala-Krishna |
| 2007/0232943 A1 | 10/2007 | Harel et al. |
| 2007/0250129 A1 | 10/2007 | Van Oort |
| 2007/0265508 A1 | 11/2007 | Sheikhzadeh-Nadjar et al. |
| 2008/0021336 A1 | 1/2008 | Dobak et al. |
| 2008/0058656 A1 | 3/2008 | Costello et al. |
| 2008/0119903 A1 | 5/2008 | Arcot-Krishnamurthy et al. |
| 2008/0140143 A1 | 6/2008 | Ettori et al. |
| 2008/0146954 A1 | 6/2008 | Bojovic et al. |
| 2008/0242976 A1 | 10/2008 | Robertson et al. |
| 2008/0269818 A1 | 10/2008 | Sullivan et al. |
| 2008/0269823 A1 | 10/2008 | Burnes et al. |
| 2008/0281195 A1 | 11/2008 | Heimdal |
| 2008/0306567 A1 | 12/2008 | Park et al. |
| 2008/0306568 A1 | 12/2008 | Ding et al. |
| 2009/0005832 A1 | 1/2009 | Zhu et al. |
| 2009/0036947 A1 | 2/2009 | Westlund et al. |
| 2009/0043352 A1 | 2/2009 | Brooke et al. |
| 2009/0048528 A1 | 2/2009 | Hopenfeld et al. |
| 2009/0053102 A2 | 2/2009 | Rudy et al. |
| 2009/0054941 A1 | 2/2009 | Eggen et al. |
| 2009/0054946 A1 | 2/2009 | Sommer et al. |
| 2009/0084382 A1 | 4/2009 | Jalde et al. |
| 2009/0093857 A1 | 4/2009 | Markowitz et al. |
| 2009/0099468 A1 | 4/2009 | Thiagalingam et al. |
| 2009/0099469 A1 | 4/2009 | Flores |
| 2009/0099619 A1 | 4/2009 | Lessmeier et al. |
| 2009/0112109 A1 | 4/2009 | Kuklik et al. |
| 2009/0143838 A1 | 6/2009 | Libbus et al. |
| 2009/0157134 A1 | 6/2009 | Ziglio et al. |
| 2009/0157136 A1 | 6/2009 | Yang et al. |
| 2009/0198298 A1 | 8/2009 | Kaiser et al. |
| 2009/0216112 A1 | 8/2009 | Assis et al. |
| 2009/0232448 A1 | 9/2009 | Barmash et al. |
| 2009/0234414 A1 | 9/2009 | Sambelashvili et al. |
| 2009/0254140 A1 | 10/2009 | Rosenberg et al. |
| 2009/0270729 A1 | 10/2009 | Corbucci et al. |
| 2009/0270937 A1 | 10/2009 | Yonce et al. |
| 2009/0299201 A1 | 12/2009 | Gunderson |
| 2009/0299423 A1 | 12/2009 | Min |
| 2009/0306732 A1 | 12/2009 | Rosenberg et al. |
| 2009/0318995 A1 | 12/2009 | Keel et al. |
| 2010/0022873 A1 | 1/2010 | Hunter et al. |
| 2010/0049063 A1 | 2/2010 | Dobak, III |
| 2010/0069987 A1 | 3/2010 | Min et al. |
| 2010/0087888 A1 | 4/2010 | Maskara |
| 2010/0094149 A1 | 4/2010 | Kohut et al. |
| 2010/0113954 A1 | 5/2010 | Zhou |
| 2010/0114229 A1 | 5/2010 | Chinchoy |
| 2010/0121403 A1 | 5/2010 | Schecter et al. |
| 2010/0145405 A1 | 6/2010 | Min et al. |
| 2010/0174137 A1 | 7/2010 | Shim |
| 2010/0198292 A1 | 8/2010 | Honeck et al. |
| 2010/0228138 A1 | 9/2010 | Chen |
| 2010/0234916 A1 | 9/2010 | Turcott et al. |
| 2010/0249622 A1 | 9/2010 | Olson |
| 2010/0254583 A1 | 10/2010 | Chan et al. |
| 2010/0268059 A1 | 10/2010 | Ryu et al. |
| 2011/0004111 A1 | 1/2011 | Gill et al. |
| 2011/0004264 A1 | 1/2011 | Siejko et al. |
| 2011/0022112 A1 | 1/2011 | Min |
| 2011/0054286 A1 | 3/2011 | Crosby |
| 2011/0054559 A1 | 3/2011 | Rosenberg et al. |
| 2011/0054560 A1 | 3/2011 | Rosenberg et al. |
| 2011/0075896 A1 | 3/2011 | Matsumoto |
| 2011/0092809 A1 | 4/2011 | Nguyen et al. |
| 2011/0112398 A1 | 5/2011 | Zarkh et al. |
| 2011/0118803 A1 | 5/2011 | Hou et al. |
| 2011/0137369 A1 | 6/2011 | Ryu et al. |
| 2011/0144510 A1 | 6/2011 | Ryu et al. |
| 2011/0172728 A1 | 7/2011 | Wang |
| 2011/0190615 A1 | 8/2011 | Phillips et al. |
| 2011/0201915 A1 | 8/2011 | Gogin et al. |
| 2011/0213260 A1 | 9/2011 | Keel et al. |
| 2011/0319954 A1 | 12/2011 | Niazi et al. |
| 2012/0004567 A1 | 1/2012 | Eberle et al. |
| 2012/0101543 A1 | 4/2012 | Demmer et al. |

(56) References Cited

U.S. PATENT DOCUMENTS

| | | |
|---|---|---|
| 2012/0101546 A1 | 4/2012 | Stadler et al. |
| 2012/0203090 A1 | 8/2012 | Min |
| 2012/0253419 A1 | 10/2012 | Rosenberg et al. |
| 2012/0283587 A1 | 11/2012 | Gosh |
| 2012/0284003 A1 | 11/2012 | Ghosh et al. |
| 2012/0296387 A1 | 11/2012 | Zhang et al. |
| 2012/0296388 A1 | 11/2012 | Zhang et al. |
| 2012/0302904 A1 | 11/2012 | Lian et al. |
| 2012/0303084 A1 | 11/2012 | Kleckner et al. |
| 2012/0310297 A1 | 12/2012 | Sweeney |
| 2012/0330179 A1 | 12/2012 | Yuk et al. |
| 2013/0006332 A1 | 1/2013 | Sommer et al. |
| 2013/0018250 A1 | 1/2013 | Caprio et al. |
| 2013/0018251 A1 | 1/2013 | Caprio et al. |
| 2013/0030491 A1 | 1/2013 | Stadler et al. |
| 2013/0060298 A1 | 3/2013 | Splett et al. |
| 2013/0072790 A1 | 3/2013 | Ludwig et al. |
| 2013/0096446 A1 | 4/2013 | Michael et al. |
| 2013/0116739 A1 | 5/2013 | Brada et al. |
| 2013/0131529 A1 | 5/2013 | Jia et al. |
| 2013/0131749 A1 | 5/2013 | Sheldon et al. |
| 2013/0131751 A1 | 5/2013 | Stadler et al. |
| 2013/0136035 A1 | 5/2013 | Bange et al. |
| 2013/0150913 A1 | 6/2013 | Bornzin et al. |
| 2013/0165983 A1 | 6/2013 | Ghosh et al. |
| 2013/0165988 A1 | 6/2013 | Ghosh |
| 2013/0261471 A1 | 10/2013 | Saha et al. |
| 2013/0261688 A1 | 10/2013 | Dong et al. |
| 2013/0289640 A1 | 10/2013 | Zhang et al. |
| 2013/0296726 A1 | 11/2013 | Niebauer et al. |
| 2013/0304407 A1 | 11/2013 | George et al. |
| 2013/0324828 A1 | 12/2013 | Nishiwaki et al. |
| 2014/0005563 A1 | 1/2014 | Ramanathan et al. |
| 2014/0018872 A1 | 1/2014 | Siejko et al. |
| 2014/0135866 A1 | 5/2014 | Ramanathan et al. |
| 2014/0135867 A1 | 5/2014 | Demmer et al. |
| 2014/0163633 A1 | 6/2014 | Ghosh et al. |
| 2014/0222099 A1 | 8/2014 | Sweeney |
| 2014/0236252 A1 | 8/2014 | Ghosh et al. |
| 2014/0276125 A1 | 9/2014 | Hou et al. |
| 2014/0277233 A1 | 9/2014 | Ghosh |
| 2014/0277245 A1 | 9/2014 | Lu |
| 2014/0323882 A1 | 10/2014 | Ghosh et al. |
| 2014/0323892 A1 | 10/2014 | Ghosh et al. |
| 2014/0323893 A1 | 10/2014 | Ghosh et al. |
| 2014/0371807 A1 | 12/2014 | Ghosh et al. |
| 2014/0371808 A1 | 12/2014 | Ghosh et al. |
| 2014/0371832 A1 | 12/2014 | Ghosh et al. |
| 2014/0371833 A1 | 12/2014 | Ghosh et al. |
| 2015/0032016 A1 | 1/2015 | Ghosh |
| 2015/0032171 A1 | 1/2015 | Ghosh |
| 2015/0032172 A1 | 1/2015 | Ghosh |
| 2015/0032173 A1 | 1/2015 | Ghosh |
| 2015/0045849 A1 | 2/2015 | Ghosh et al. |
| 2015/0142069 A1 | 5/2015 | Sambelashvili |
| 2015/0157225 A1 | 6/2015 | Gillberg et al. |
| 2015/0157231 A1 | 6/2015 | Gillberg et al. |
| 2015/0157232 A1 | 6/2015 | Gillberg et al. |
| 2015/0157865 A1 | 6/2015 | Gillberg et al. |
| 2015/0216434 A1 | 8/2015 | Ghosh et al. |
| 2015/0265840 A1 | 9/2015 | Ghosh et al. |
| 2016/0030747 A1 | 2/2016 | Thakur et al. |
| 2016/0030751 A1 | 2/2016 | Ghosh et al. |
| 2016/0045737 A1 | 2/2016 | Ghosh et al. |
| 2016/0045738 A1 | 2/2016 | Ghosh et al. |
| 2016/0045744 A1 | 2/2016 | Gillberg et al. |
| 2016/0184590 A1 | 6/2016 | Ghosh |
| 2016/0213928 A1 | 7/2016 | Ghosh |
| 2016/0331258 A1 | 11/2016 | Du et al. |
| 2017/0246460 A1 | 8/2017 | Ghosh |
| 2017/0246461 A1 | 8/2017 | Ghosh |
| 2017/0143976 A1 | 11/2017 | Tazawa et al. |
| 2018/0263522 A1 | 9/2018 | Ghosh et al. |
| 2018/0264258 A1 | 9/2018 | Cheng et al. |

FOREIGN PATENT DOCUMENTS

| | | |
|---|---|---|
| CN | 1878595 A | 12/2006 |
| CN | 101073502 A | 11/2007 |
| EP | 1 072 284 A2 | 1/2001 |
| EP | 1 504 713 A1 | 2/2005 |
| EP | 2 016 976 A1 | 1/2009 |
| EP | 2 391 270 A1 | 7/2011 |
| EP | 1 925 337 B1 | 3/2012 |
| EP | 2 436 309 A2 | 4/2012 |
| EP | 2 435 132 B1 | 8/2013 |
| WO | WO 1998/026712 A1 | 6/1998 |
| WO | WO 1999/006112 A1 | 2/1999 |
| WO | WO 2000/045700 A1 | 8/2000 |
| WO | WO 2001/067950 A1 | 9/2001 |
| WO | WO 2003/070323 A1 | 8/2003 |
| WO | WO 2005/056108 A2 | 6/2005 |
| WO | WO 2006/069215 A2 | 6/2006 |
| WO | WO 2006/105474 A2 | 10/2006 |
| WO | WO 2006/115777 A1 | 11/2006 |
| WO | WO 2006/117773 A1 | 11/2006 |
| WO | WO 2007/013994 A2 | 2/2007 |
| WO | WO 2007/027940 A2 | 3/2007 |
| WO | WO 2007/013994 A3 | 4/2007 |
| WO | WO 2007/027940 A3 | 6/2007 |
| WO | WO 2007/139456 A1 | 12/2007 |
| WO | WO 2008/151077 A2 | 12/2008 |
| WO | WO 2006/069215 A3 | 6/2009 |
| WO | WO 2009/079344 A1 | 6/2009 |
| WO | WO 2009/139911 A2 | 11/2009 |
| WO | WO 2009/148429 A1 | 12/2009 |
| WO | WO 2010/019494 A1 | 2/2010 |
| WO | WO 2010/071520 A1 | 6/2010 |
| WO | WO 2010/088040 A1 | 8/2010 |
| WO | WO 2010/088485 A1 | 8/2010 |
| WO | WO 2011/070166 A1 | 6/2011 |
| WO | WO 2011/090622 A1 | 7/2011 |
| WO | WO 2011/099992 A1 | 8/2011 |
| WO | WO 2012/037471 A2 | 3/2012 |
| WO | WO 2012/037471 A3 | 6/2012 |
| WO | WO 2012/106297 A2 | 8/2012 |
| WO | WO 2012/106297 A3 | 8/2012 |
| WO | WO 2012/109618 A2 | 8/2012 |
| WO | WO 2012/110940 A1 | 8/2012 |
| WO | WO 2012/109618 A3 | 11/2012 |
| WO | WO 2012/151364 A1 | 11/2012 |
| WO | WO 2012/151389 A1 | 11/2012 |
| WO | WO 2013/006724 A2 | 1/2013 |
| WO | WO 2013/010165 A1 | 1/2013 |
| WO | WO 2013/010184 A1 | 1/2013 |
| WO | WO 2013/006724 A3 | 4/2013 |
| WO | WO 2014/179454 A1 | 11/2014 |
| WO | WO 2014/179459 A2 | 11/2014 |
| WO | WO 2014/179459 A3 | 1/2015 |
| WO | WO 2015/013271 A1 | 1/2015 |
| WO | WO 2015/013493 A1 | 1/2015 |
| WO | WO 2015/013574 A1 | 1/2015 |

OTHER PUBLICATIONS

International Search Report and Written Opinion dated May 3, 2012 for International Application No. PCT/US2012/036302; 9 pages.
International Search Report and Written Opinion dated Aug. 6, 2014 for International Application No. PCT/US2014/036153; 14 pages.
International Search Report and Written Opinion dated Nov. 7, 2014 for International Application No. PCT/US2014/036163; 12 pages.
International Search Report and Written Opinion dated Oct. 28, 2014 for International Application No. PCT/US2014/041928; 15 pages.
International Search Report and Written Opinion dated Oct. 24, 2014 for International Application No. PCT/US2014/041929; 14 pages.
International Search Report and Written Opinion dated Nov. 4, 2014 for International Application No. PCT/US2014/0247583; 7 pages.
International Search Report and Written Opinion dated Nov. 12, 2014 for International Application No. PCT/US2014/047971; 7 pages.

(56) References Cited

OTHER PUBLICATIONS

International Search Report and Written Opinion dated Nov. 12, 2014 for International Application No. PCT/US2014/048120; 7 pages.
International Search Report and Written Opinion dated Mar. 9, 2015 for International Application No. PCT/US2014/069214; 11 pages.
International Search Report and Written Opinion dated Mar. 17, 2015, for International Application No. PCT/US2014/069192; 11 pages.
International Search Report and Written Opinion dated Mar. 16, 2015 for International Application No. PCT/US2014/069182; 11 pages.
International Search Report and Written Opinion dated Apr. 8, 2015 for International Application No. PCT/US2014/069070; 11 pages.
International Search Report and Written Opinion dated Jun. 11, 2015 for International Application No. PCT/US2015/021442; 13 pages.
Biffi et al., "Occurrence of Phrenic Nerve Stimulation in Cardiac Resynchronization Therapy Patients: the Role of Left Ventricular Lead Type and Placement Site," *Europace*, 2013; 15:77-82.
Botker MD, PhD., et al., "Electromechanical Mapping for Detection of Myocardial Viability in Patients with ischemia Cardiomyopathy," Circulation, Mar. 2001; vol. 103, No. 12, pp.
"CardioGuide System Enables Real-Time Navigation of Left Ventricular Leads During Medtronic CRT Implants," Press Release, Apr. 9, 2013, Medtronic, Inc., 2 pgs.
Cuculich, P.S., et al., "The Electrophysiological Cardiac Ventricular Substrate in Patients After Myocardial Infection" J. Am. Coll. Cardiol. 2011; 58:1893-1902.
Czerwinska et al., "Method of Segmentation of Thorax Organs Images Applied to Modeling the Cardiac Electrical Field," *Engineering in Medicine and Biology Society*, Proceedings of the $22^{nd}$ Annual International Conference of the IEEE, vol. 1, 23, Jul. 23, 2000.; pp. 402-405.
Dawoud, F. et al., "Inverse Electrocardiographic Imaging to Assess Electrical Dyssynchrony in Cardiac Resynchronization Therapy Patients," Computing in Cardiology, 2012; 39:993-996.
Freund et al., "A Decision-Theoretic Generalization of Online Learning and an Application to Boosting," *Journal of Computer and System Sciences*, 1997; 55(1):119-139.
Friedman, "Greedy Function Approximation: A Gradient Boosting Machine," *Annals of Statistics*, 2001; 29(5):1189-1232.
Friedman, "Stochastic Gradient Boosting," *Computational Statistics and Data Analysis*, 2002; 38(4):367-378.
Friedman et al., "Additive Logistic Regression: a Statistical View of Boosting," *Annals of Statistics*, 2000; 28(2):337-374.
Fung et al., Chapter 20, Optimization of Cardiac Resynchronization Therapy, Cardiac Resynchronization Therapy, Second Edition, Copyright 2008, Blackwell Publishing Ltd., pp. 356-373.
Ghosh et al. "Accuracy of Quadratic Versus Linear Interpolation in Noninvasive Electrocardiographic Imaging (ECGI)," *Annuals of Biomedical Engineering*, vol. 33, No. 9. Sep. 2005; pp. 1187-1201.
Ghosh et al., "Cardiac Memory in Patents with Wolff-Parkinson-White Syndrome: Noninvasive Imaging of Activation and Repolarization Before and After Catheter Ablation" *Circulation*, 2008; 118:907-915. Published online Aug. 12, 2008.
Ghosh et al. "Application of L1-Norm Regularization to Epicardial Potential Solution of the Inverse Electrocardiography Problem," *Annuals of Biomedical Engineering*, vol. 37, No. 5, May 2009; pp. 902-912.
Ghosh et al., "Electrophysiological Substrate and Intraventricular LV Dyssynchrony in Non-ischemic Heart Failure Patients Undergoing Cardiac Resynchronization Therapy," *Heart rhythm : the official journal of the Heart Rhythm Society*, 2011; 8(5):692-699.
Gold et al., "Comparison of Stimulation Sites within Left Ventricular Veins on the Acute Hemodynamic Effects of Cardiac Resynchronization Therapy" *Heart Rhythm*, Apr. 2005; 2(4):376-381.
Gulrajani, "The Forward and Inverse Problems of Electrocardiography," *IEEE Engineering in Medicine and Biology*, IEEE Service Center, vol. 17, No. 5, Sep. 1, 1988; pp. 84-101, 122.
Hansen, "Regularization Tools: A Matlab Package for Analysis and Solution of Discrete Ill-Posed Problems," Version 4.1 for Matlab 7.3; Mar. 2008; 128 pages. Retrieved from the Internet: Jun. 19, 2014 http://www.mathworks.com/matlabcentral/fileexchange/52-regtools.
Hayes et al., "Cardiac Resynchronization Therapy and the Relationship of Percent Biventricular Pacing to Symptoms and Survival," *Heart Rhythm*, Sep. 2011; 8(9): 1469-1475.
"Heart Failure Management" datasheet [online]. Medtronic, Minneapolis, Minnesota, [Last updated on Jun. 3, 2013].Retrieved from the Internet: www.medtronic.com; 9 pages.
Hopenfeld et al., "The Effect of Conductivity on ST-Segment Epicardial Potentials Arising from Subendocardial Ischemia," Annals of Biomedical Eng., Jun. 2005; vol. 33, No. 6, pp. 751-763.
Jia et al., "Electrocardiographic Imaging of Cardiac Resynchronization Therapy in Heart Failure: Observation of Variable Electrophysiologic Responses," *Heart Rhythm*, vol. 3, No. 3; Mar. 1, 2006, pp. 296-310.
Kornreich, "Body Surface Potential Mapping of ST Segment Changes in Acute Myocardial Infarction," *Circulation*, 1993; 87: 773-782.
Lumason™, Brochure, Bracco Diagnostocs. Oct. 2014.
Medtronic Vitatron Carelink Encore® Programmer Model 29901 Reference Manual, 2013, Medtronic, Inc., Minneapolis, MN.
Miri et al., "Applicability of body surface potential map in computerized optimization of biventricular pacing," Annals of Biomedical Engineering, vol. 38, No. 3, Mar. 2010, pp. 865-875.
Miri et al., "Comparison of the electrophysiologically based optimization methods with different pacing parameters in patient undergoing resynchronization treatment," 30th Annual International IEEE EMBS Conference, Aug. 2008, pp. 1741-1744.
Miri et al., "Computerized Optimization of Biventricular Pacing Using Body Surface Potential Map," 31st Annual International Conference of the IEEE EMBS, Sep. 2009, pp. 2815-2818.
Miri et al., "Efficiency of Timing Delays and Electrode Positions in Optimization of Biventricular Pacing: A Simulation Study," IEEE Transactions on Biomedical Engineering, Nov. 2009, pp. 2573-2582.
Modre et al., "Noninvasive Myocardial Activation Time Imaging: A Novel Inverse Algorithm Applied to Clinical ECG Mapping Data" *IEEE Transactions on Biomedical Engineering*, vol. 49; No. 10, Oct. 2002; pp. 1153-1161.
Nash et al., "An Experimental-Computational Framework for Validating in-vivo ECG Inverse Algorithms," International Journal of Bioelectromagnetism, vol. 2, No. 2, Dec. 31, 2000, 9 pp.
Potse et al., "Mathematical Modeling and Simulation of Ventricular Activation Sequences: Implications for Cardiac Resynchronization Therapy," *J. of Cardiovasc. Trans. Res.*, 2012; 5:146-158.
Prinzen et al., "Cardiac Resynchronization Therapy State-of-the-Art of Current Applications, Guidelines, Ongoing Trials, and Areas of Controversy" *Circulation*, 2013; 128: 2407-2418.
Ridgeway, "The State of Boosting," *Computing Science and Statistics*, 1999; 31:172-181.
Ryu et al., "Simultaneous Electrical and Mechanical Mapping Using 3D Cardiac Mapping System: Novel Approach for Optimal Cardiac Resynchronization Therapy," *Journal of Cardiovascular Electrophysiology*, Feb. 2010; 21(2):219-22.
Silva et al., "Cardiac Resynchronization Therapy in Pediatric Congenital Heart Disease: Insights from Noninvasive Electrocardiographic Imaging" *Heart Rhythm*, vol. 6, No. 8. Aug. 1, 2009; pp. 1178-1185.
Singh et al., "Left Ventricular Lead Position and Clinical Outcome in the Multicenter Automatic Defibrillator Implantation Trial-Cardiac Resynchronization Therapy (MADIT-CRT) Trial," *Circulation*, 2011; 123:1159-1166.
Sperzel et al., "Intraoperative Characterization of Interventricular Mechanical Dyssynchrony Using Electroanatomic Mapping System—A Feasibility Study," *Journal of Interventional Cardiac Electrophysiology*, Nov. 2012; 35(2):189-96.
Steinhaus BM., "Estimating cardiac transmembrane activation and recovery times from unipolar and bipolar extracellular electrograms: a simulation study," Circulation Research, 1989, 64:449-462.

(56) References Cited

OTHER PUBLICATIONS

Strik et al., "Electrical and Mechanical Ventricular Activation During Left Bundle Branch Block and Resynchronization," *J. of Cardiovasc. Trans. Res.*, 2012; 5:117-126.

Svendsen et al., "Computational Models of Cardiac Electrical Activation," Chapter 5, Computational Nov. 2010, pp. 73-88.

Sweeney et al., "Analysis of Ventricular Activation Using Surface Electrocardiography to Predict Left Ventricular Reverse Volumetric Remodeling During Cardiac Resynchronization Therapy," *Circulation*, Feb. 9, 2010;121(5):626-34. Available online Jan. 25, 2010.

Sweeney et al., QRS Fusion Complex Analysis Using Wave Interference to Predict Reverse Remodeling During Cardiac Resynchronization Therapy, heart Rhythm, 2014, 11:806-813.

Turner et al, "Electrical and Mechanical Components of Dyssynchrony in Heart Failure Patients with Normal QRS Duration and Left Bundle-Branch Block," *Circulation* 2004; 109: 2544-2549.

Van Deursen et al., "Vectorcardiography as a Tool for Easy Optimization of Cardiac Resynchronization Therapy in Canine LBBB Hearts," *Circulation Arrhythmia and Electrophysiology*, Jun. 1, 2012; 5(3):544-52. Available online Apr. 24, 2012.

Vardas et al., The Task Force for Cardiac Pacing and Cardiac Resynchronization Therapy of the European Society of Cardiology. Developed in Collaboration with the European Heart Rhythm Association, *European Heart Journal*, 2007; 28:2256-2295.

Varma et al., "Placebo CRT," *Journal of Cardiovascular Electrophysiology*, vol. 19, Aug. 2008; p. 878.

Wang et al., "Application of the Method of Fundamental Solutions to Potential-based Inverse Electrocardiography," Annals of Biomedical Engineering, Aug. 2006, pp. 1272-1288.

Wellens, MD et al., "The Electrocardiogram 102 Years After Einthoven," Circulation, Feb. 2004; vol. 109, No. 5, pp. 562-564.

Williams et al., "Short-Term Hemodynamic Effects of Cardiac Resynchronization Therapy in Patients With Heart Failure, a Narrow QRS Duration, and No Dyssynchrony," *Circulation*, Oct. 27, 2009; 120: 1687-1694.

CRITERIA FOR DETERMINATION OF LOCAL TISSUE LATENCY NEAR PACING ELECTRODE

TECHNICAL FIELD

The disclosure relates generally to optimizing control parameters during cardiac pacing therapies; and, more particularly, to optimizing pacing therapy control parameters based on determining the presence of local tissue latency near pacing electrodes.

BACKGROUND

A wide variety of implantable medical devices for delivering a therapy or monitoring a physiologic condition have been clinically implanted or proposed for clinical implantation in patients. Some implantable medical devices may employ one or more elongated electrical leads and/or sensors. In some cases, implantable medical devices deliver electrical stimulation therapy and/or monitor physiological signals via one or more electrodes or sensor elements, which may be included as part of one or more elongated implantable medical leads. Implantable medical leads may be configured to allow electrodes or sensors to be positioned at desired locations for delivery of stimulation or sensing. For example, electrodes or sensors may be located at a distal portion of the lead. A proximal portion of the lead may be coupled to an implantable medical device housing, which may contain electronic circuitry such as stimulation generation and/or sensing circuitry.

Implantable medical devices can be configured to deliver cardiac therapy such as cardiac resynchronization therapy (CRT) to treat patients suffering from congestive heart failure. CRT involves either delivering pacing stimulus to both ventricles or to one ventricle with the desired result of a more or less simultaneous mechanical contraction and ejection of blood from the ventricles. Delivering pacing stimulus to both ventricles is referred to as biventricular pacing (BV) while monoventricular pacing refers to left ventricular (LV) pacing, or right ventricular (RV) only pacing, often with fusion from intrinsic conduction if there is intact atrio-ventricular conduction.

CRT improves heart chamber synchrony. Improved heart chamber synchrony may enhance hemodynamic performance of the heart thereby alleviating symptoms of congestive heart failure. Exemplary hemodynamic parameters include ventricular pressure and/or the rate of change in ventricular pressure. Achieving a positive clinical benefit from CRT is dependent on several therapy control parameters, such as the atrio-ventricular (AV) delay and the inter-ventricular (VV) delay. The AV delay controls the timing of ventricular pacing pulses relative to an atrial depolarization, intrinsic or paced. The VV delay controls the timing of a pacing pulse in one ventricle relative to a paced or intrinsic sensed event in the other ventricle.

Selecting optimal AV and VV delays for use in controlling CRT pacing pulses may be affected by local tissue latency. Local tissue latency involves the substantially delayed response time to pace stimulation that occurs at the pace/sense lead electrode to tissue interface. Local tissue latency may be caused by diseased substrate (e.g. scar, fibrosis, etc.) or local conduction block around the site of the pacing electrode. Local tissue latency may have important implications for CRT pacing therapies. For example, if there is latency in a LV lead, it may result in simultaneous BV pacing thereby appearing as RV only pacing which is not as beneficial for the patient. A need remains, therefore, for a device and method that detects local tissue latency and, in response, adjusts one or more CRT pacing control parameters.

SUMMARY

The present disclosure is directed toward techniques for detection of local tissue latency near pacing electrodes; and, in response to whether local tissue latency is detected, adjusting a pacing control parameter for delivery of pacing therapy in order to improve synchrony between the atria and the ventricles and/or between the left and right ventricles. Determination of local tissue latency is made by an implantable medical device processor evaluating timing relationships of fiducial points on an electrogram (EGM) signal in response to pacing at short atrioventricular delays. Fiducial is a reference point on a signal in a cardiac cycle. The reference time point may be an atrial or ventricular sensed or paced event, an R-wave sensed in the RV or a fiducial point. The fiducial may be the onset of QRS (e.g. a QRS complex sensed in the RV) the peak of QRS (e.g. minimum values, minimum slopes, maximum slopes), zero crossings, threshold crossings, etc. of a near or far-field EGM), onset of application of a pacing electrical stimulus, or the like.

In response to determination of local tissue latency, a control parameter such as a timing parameter, e.g., an atrio-ventricular (AV) delay or an inter-ventricular (VV) delay, is controlled by an implantable medical device (IMD) processor to compensate for the delay caused by tissue latency. The fiducials on the EGM signal includes a minimum time (Tmin) associated with the minimum amplitude (Min) and a maximum time (Tmax) associated with the maximum amplitude. The IMD processor can determine whether tissue latency exists at an electrode. The IMD processor can determine tissue latency relative to a pacing electrode in response to evaluating one or more latency conditions. Once latency condition relates to determining whether (Maxamp−Minamp|/|Tmax−Tmin|) is less than a predetermined ratio. A determination is then made as to whether to adjust one or more control pacing parameters, in response to determining whether (|Maxamp−Minamp|/|Tmax−Tmin|) is less than the predetermined ratio, wherein the control pacing parameters being one of AV delay, inter-ventricular (VV) delay, pacing vector, and pacing output.

Another exemplary latency condition relates to whether the Minamp is less than a prespecified amplitude threshold when the other EGM parameters satisfy conditions of effective capture as described below. An exemplary prespecified amplitude threshold can be in the range of about 3.5 to about 5 millivolts (mV). It should be appreciated that the IMD processor can evaluate one latency condition and/or both latency conditions when determining whether tissue latency near a pacing electrode is present.

The present disclosure may be able to achieve increased sensitivity for determining tissue latency near a pacing electrode. Additionally, during implant of a medical device, the present disclosure graphically displays a latency flag on an electrode of a multipolar lead during the implantable medical device performing automated routines of electrically testing each electrode of a set of electrodes. For example, one electrode is paced while the remaining electrodes are used to sense the response from cardiac tissue to the delivered pace. By cycling through each electrode of the set of electrodes for pacing, data acquired during each pacing operation can be displayed on a graphical user interface of a programmer to the user.

The details of one or more aspects of the disclosure are set forth in the accompanying drawings and the description below. Other features, objects, and advantages will be apparent from the description and drawings, and from the claims.

DETAILED DESCRIPTION

Figure 1:
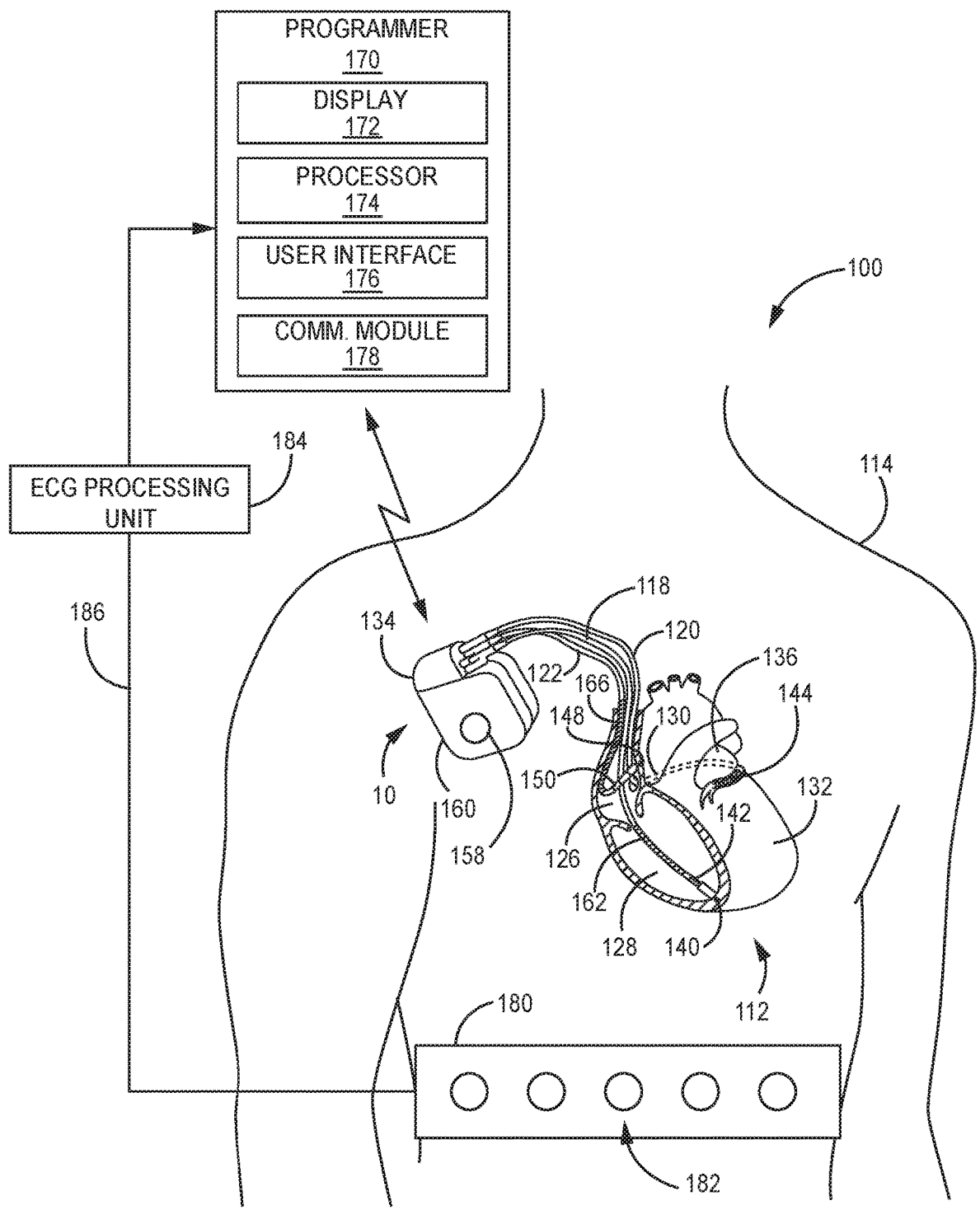
FIG. 1 is a schematic diagram of one embodiment of an implantable medical device (IMD) system in which techniques disclosed herein may be implemented.

Cardiac resynchronization therapy (CRT) alters electrical activation of the ventricles, improving spatial synchronization of electrical conduction in hearts with electrical conduction disorders such as left bundle branch block, right bundle branch block or other disorders. Optimal electrical activation of the heart may therefore be important for CRT efficacy. Optimal electrical activation can depend on a number of factors including the location of the pacing electrodes and pacing timing parameters such as AV delay and VV delay.

In one or more embodiments, a multipolar electrical lead is employed to deliver CRT to the left ventricle (LV). The multipolar lead comprises at least four electrodes. An exemplary multipolar lead includes a quadripolar lead such as the ATTAIN PERFORMA™ commercially available from Medtronic Inc., located in Minneapolis, Minn. Each electrode of a multipolar lead paces cardiac tissue at a short AV delay (e.g. less than 60 ms) with sufficient energy for LV capture while the remaining LV electrodes sense the cardiac tissue response (e.g. intracardiac electrogram (EGM) signals) from the delivered pacing pulses. Fiducials such as minimum amplitude (Minamp), minimum time (Tmin) associated with Minamp, maximum amplitude (Maxamp) and its associated maximum timing (Tmax) of an EGM corresponding to each cycle of ventricular pacing are acquired by the processor in an implantable medical device and/or processor for the programmer. Cycle of ventricular pacing is defined as one paced cardiac cycle or beat. The processor in the IMD or the processor can evaluate one or more tissue latency conditions after ventricular tissue is paced. In one or more embodiments, tissue latency exists with a LV electrode when Minamp is less than a prespecified amplitude threshold while the EGM parameters satisfying conditions of effective capture during LV only pacing or the ratio of (|Maxamp−Minamp|/|Tmax−Tmin|) is less than a predetermined ratio while the EGM parameters do not satisfy conditions of effective capture during simultaneous biventricular pacing, where the aforementioned EGM parameters are measured for the vector from LV cathode to RV Coil or LV cathode to Can (i.e. housing for the IMD) while pacing under ideal conditions of tissue capture (e.g. sufficient pacing outputs, short AV delay, overdriving intrinsic heart rate). The LV electrode is flagged with a latency indicator and then displayed on the user interface of the programmer. Effective capture is described in U.S. Pat. No. 8,750,998 filed Dec. 6, 2012 and entitled EFFECTIVE CAPTURE TEST and US 2014-0277245 A1 filed Mar. 15, 2013 entitled and MODULATE PACING RATE TO INCREASE THE PERCENTAGE OF EFFECTIVE VENTRICULAR CAPTURE DURING ATRIAL FIBRILLATION, both of which are incorporated by reference in their entirety. Displaying the latency indicator on a graphical user interface can include a medical electrical lead (e.g. a quadripolar lead) in which four electrodes at the distal end of the lead are displayed with one electrode shown "X" out, shaded out and unable to be selected for pacing, and/or data indicating that the particular electrode is associated with tissue latency. Other results displayed on the user interface includes pacing thresholds, impedances, impact on longevity. Techniques disclosed herein enable an IMD to perform closed loop optimization of electrical activation of the heart.

FIG. 1 is a schematic diagram of one embodiment of an implantable medical device (IMD) system 100 in which techniques disclosed herein may be implemented to provide therapy to heart 112 of patient 114. System 100 includes IMD 10 coupled to leads 118, 120, and 122 which carry multiple electrodes. IMD 10 is configured for bidirectional communication with programmer 170. IMD 10 may be, for example, an implantable pacemaker or implantable cardioverter defibrillator (ICD) that provides electrical signals to heart 112 via electrodes coupled to one or more of leads 118, 120, and 122 for pacing, cardioverting and defibrillating the heart 112. IMD 10 is capable of delivering pacing in one or more heart chambers, and in the embodiment shown, is configured for multi-chamber pacing and sensing in the right atrium (RA) 126, the right ventricle (RV) 128, and the left ventricle (LV) 132 using leads 118, 120 and 122.

IMD 10 delivers RV pacing pulses and senses RV intracardiac electrogram (EGM) signals using RV tip electrode 140 and RV ring electrode 142. RV lead 118 is shown to carry a coil electrode 162 which may be used for delivering high voltage cardioversion or defibrillation shock pulses. IMD 10 senses LV EGM signals and delivers LV pacing pulses using the electrodes 144 carried by a multipolar coronary sinus lead 120, extending through the RA 126 and into a cardiac vein 130 via the coronary sinus. In some embodiments, coronary sinus lead 120 may include electrodes positioned along the left atrium (LA) 136 for sensing left atrial (LA) EGM signals and delivering LA pacing pulses.

IMD 10 senses RA EGM signals and delivers RA pacing pulses using RA lead 122, carrying tip electrode 148 and ring electrode 150. RA lead 122 is shown to be carrying coil electrode 166 which may be positioned along the superior vena cava (SVC) for use in delivering cardioversion/defibrillation shocks. In other embodiments, RV lead 118 carries both the RV coil electrode 162 and the SVC coil electrode 166. IMD 10 is configured to detect tachyarrhythmias of heart 112, such as fibrillation of ventricles 128 and 132, and deliver high voltage cardioversion or defibrillation therapy to heart 112 in the form of electrical shock pulses. Pacing and sensing of the cardiac chambers is typically achieved using the pace/sense electrodes 140, 142, 144 148 and 150, however in some embodiments coil electrodes 162 and/or 166 may be used in sensing and/or pacing electrode vectors.

While IMD 10 is shown in a right pectoral implant position in FIG. 1, a more typical implant position, particularly when IMD 10 is embodied as an ICD, is a left pectoral implant position. In other embodiments, IMD 10 may be implanted in an abdominal location or substernally as a subcutaneous device as shown and described in U.S. Pat. No. 9,768,319 to Sambelashvii incorporated by reference in its entirety.

IMD 10 includes internal circuitry for performing the functions attributed to IMD 10. Housing 160 encloses the internal circuitry. It is recognized that the housing 160 or portions thereof may be configured as an active electrode 158 for use in cardioversion/defibrillation shock delivery or used as an indifferent electrode for unipolar pacing or sensing configurations with any electrodes carried by leads 118, 120 and 122. IMD 10 includes a connector block 134 having connector bores for receiving proximal lead connectors of leads 118, 120 and 122. Electrical connection of electrodes carried by leads 118, 120 and 122 and IMD internal circuitry is achieved via various connectors and electrical feedthroughs included in connector block 134.

IMD 10 is configured for delivering CRT by delivering pacing pulses in one or both ventricles 128 and 132 for controlling and improving ventricular synchrony. LV pacing may be delivered using a selected pacing vector that utilizes at least one electrode 144 on multipolar LV lead 120. RV pacing is delivered using RV tip electrode 140 and ring electrode 142. CRT may be delivered by pacing in a single ventricular chamber (LV or RV) or both chambers (biventricular pacing) depending on patient need. The methods described herein are implemented in a dual or multi-chamber pacemaker or ICD delivering pacing pulses to the right and/or left ventricles using programmable pacing pulse timing parameters and selected pacing vectors.

In some embodiments, IMD 10 is configured to provide "adaptive CRT" which automatically switches between biventricular pacing and LV-only pacing in response to changes in the patient's intrinsic AV conduction. When AV conduction is impaired or blocked, or more generally when AV conduction time is slowed, biventricular pacing is delivered. When normal AV conduction returns, LV-only pacing is delivered. In this way, RV pacing is delivered only when needed based on the patient's own AV conduction status, which may fluctuate over time.

While a multi-chamber ICD is shown in FIG. 1, it is recognized that techniques disclosed herein may be implemented in a single chamber, dual chamber or multi-chamber pacemaker, with or without anti-arrhythmia therapies such as cardioversion and defibrillation shock capabilities. For example, techniques disclosed herein for closed-loop optimization of a CRT control parameter may be used to optimize the AV delay applied between an atrial event, sensed or paced, and a ventricular pacing pulse delivered in one ventricle (RV or LV only) or biventricular pacing pulses (RV and LV).

Figure 9:
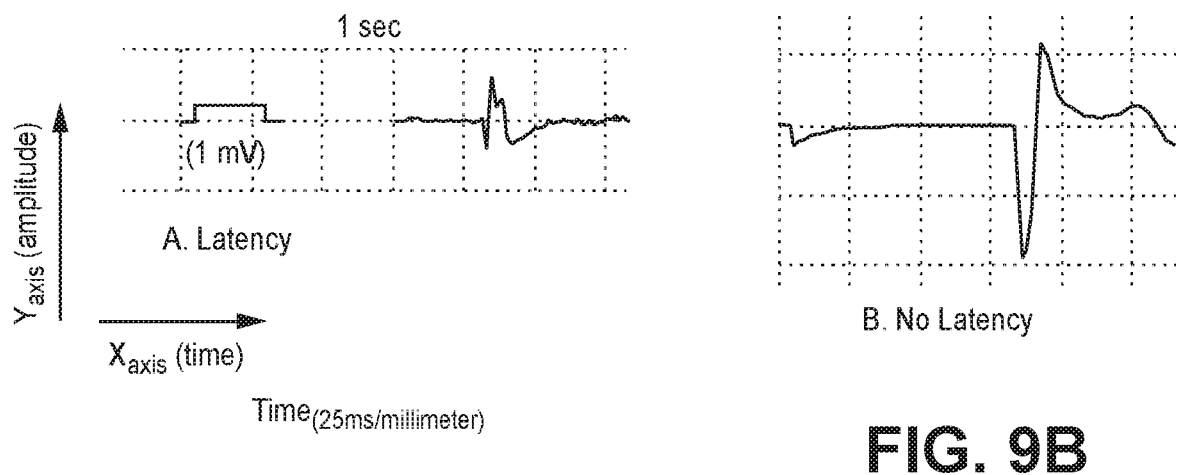
FIG. 9A depicts an exemplary EGM signal, exhibiting local LV tissue latency, that was acquired from the LV cathode to RV Coil during LV only pacing at a short AV delay (e.g. less than 60 ms) from the LV cathode.
FIG. 9B depicts an exemplary EGM signal that does not exhibit local LV tissue latency while using the same vector and similar conditions of LV only pacing as FIG. 9A.
Figure 10:
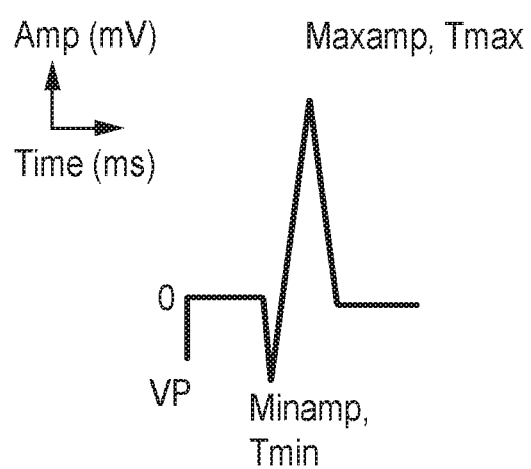
FIG. 10 depicts a schematic EGM signal that shows the pacing pulse, a minimum amplitude, a maximum amplitude, and their respective timing Tmin and Tmax in which the timing intervals may be measured with respect to a common time-reference (e.g. time at which ventricular pacing is delivered).

Programmer 170 includes a display 172, a processor 174, a user interface 176, and a communication module 178 including wireless telemetry circuitry for communication with IMD 10. In some examples, programmer 170 may be a handheld device or a microprocessor-based home monitor or bedside programming device. A user, such as a physician, technician, nurse or other clinician, may interact with programmer 170 to communicate with IMD 10. For example, the user may interact with programmer 170 via user interface 176 to retrieve currently programmed operating parameters, physiological data collected by IMD 10, or device-related diagnostic information from IMD 10. A user may also interact with programmer 170 to program IMD 10, e.g., select values for operating parameters of the IMD. A user interacting with programmer 170 can initiate a CRT optimization procedure performed by IMD 10 automatically or semi-automatically, to establish data for closed-loop optimization of CRT control parameters. The EGM signal is sensed by IMD 10 using selected cardiac electrodes 140, 142, 144, 162, 166 and/or housing electrode 158. The EGM data are typically determined during CRT as it is delivered using varying parameter settings used to determine conduction through the cardiac tissue. By evaluating conduction through cardiac tissue response to pacing stimulus, a determination can be made as to whether local tissue latency is present. An example of an EGM signal exhibiting tissue latency is shown in FIG. 9A. As shown, the EGM includes an amplitude along the y-axis and time along the x-axis (measured in 25 millisonds per millimeter). The amplitude is not as important as the time measured along the x-axis. The EGM depicted in FIG. 9A is shown as being narrower than the example of an EGM signal that does not exhibit tissue latency shown in FIG. 9B. The EGM of FIG. 9B clearly depicts a wave that has features that are wider compared to the features of the EGM in FIG. 9A along the x-axis. Delivering pacing pulses to one or more ventricles, without latency, optimizes synchrony between the atria and ventricles to achieve improved cardiac function. Additionally, or alternatively, delivering pacing pulses to one or more ventricles, without latency, optimizes synchrony between the ventricles. Each EGM was acquired from an LV electrode on a quadripolar lead (e.g. ATTAIN PERFORMA™ commercially available from Medtronic, Inc. located in Minneapolis, Minn.) and a RV coil during LV only pacing at a short AV delay during LV only pacing.

If local tissue latency was determined to be present, control parameters (e.g. AV delay, VV delay, pacing vector, pacing output etc.) can be adjusted and/or optimized by IMD 10 in a closed loop manner. The programmer 170 is also configured to determine whether local tissue latency is present and adjust control parameters while the patient is in a clinical setting. Knowledge of a patient-specific optimal electrical condition is established using intracardiac electrodes to acquire EGM signals and/or surface electrocardiogram (ECG) electrode signals using skin electrodes in which to detect a distinctive delay between the pacing artifact (i.e. spike) and the onset of QRS. The ECG and/or the EGM is recorded for a CRT parameter setting (shortened AV delay such as 60 ms, VV delay). The EGM signal includes a minimum time (Tmin) associated with the minimum amplitude (Min) within a pre-specified time period (e.g. 160 ms, 170 ms, 180 ms, 190 ms, 200 ms etc.)

Programmer 170 includes a communication module 178 to enable wireless communication with IMD 10. Examples of communication techniques used by system 100 include low frequency or radiofrequency (RF) telemetry, which may be an RF link established via Bluetooth, WiFi, or MICS, for example as described in U.S. Pat. No. 5,683,432 (Goedeke et al). In some examples, programmer 170 may include a programming head that is placed proximate to the patient's body near the IMD 10 implant site, and in other examples programmer 170 and IMD 10 may be configured to communicate using a distance telemetry algorithm and circuitry that does not require the use of a programming head and does not require user intervention to maintain a communication link.

It is contemplated that programmer 170 may be coupled to a communications network via communications module 178 for transferring data to a remote database or computer to allow remote monitoring and management of patient 114 using the techniques described herein. Remote patient management systems may be configured to utilize the presently disclosed techniques to enable a clinician to review CRT therapy parameters and authorize programming of IMD 10. Reference is made to commonly-assigned U.S. Pat. No. 6,599,250 (Webb et al.), U.S. Pat. No. 6,442,433 (Linberg et al.), U.S. Pat. No. 6,418,346 (Nelson et al.), and U.S. Pat. No. 6,480,745 (Nelson et al.) for general descriptions and examples of network communication systems for use with implantable medical devices for remote patient monitoring and device programming, all of which patents are hereby incorporated herein by reference in their entirety.

While the present disclosure contemplates EGMs, acquired from intracardiac electrodes, being used to implement closed loop features of the disclosure, ECGs can also be used when implanting IMD 10 and/or during follow-up visits to the hospitals to optimize control parameters as described herein. To acquire ECGs, system 100 can further include an array of surface electrodes 182, which may be carried by a belt or strap 180 adapted to be wrapped around the torso of patient 114 to position electrodes 182 in the vicinity of heart 112. Strap 180 is shown inferior to heart 112 in FIG. 1, but it is understood that belt 180 may be positioned in a relatively more superior position to surround heart 112 such that electrodes 180 are positioned nearer to heart 112. Electrodes 182 are used to acquire surface signals from heart 112 during a CRT optimization session. A CRT control parameter (e.g. AV delay, VV delay, pacing vector, pacing output etc.) may be optimized by adjusting the parameter until the surface ECG-based determinations of ventricular activation indicate optimally synchronized ventricular activation. In one or more embodiments, EGM data is then generated by IMD 10 at the optimized parameter setting and multiple increments/decrements from the optimal delay setting to establish EGM-based local tissue latency data and its relationship to increments or decrements (e.g. 5 ms, 10 ms, 15 ms, 20 ms, 30 ms, 40 ms etc.) from optimal control parameter settings, specific to the patient. The EGM-based data is used by IMD 10 to adjust the control parameter in a closed loop to maintain optimized ventricular activation in response to detection of local tissue latency.

In one example illustrated in FIG. 1, strap 180 is wrapped around the torso of patient 114 such that the electrodes 182 surround heart 112. Electrodes 182 may be positioned around the circumference of patient 114, including the posterior, lateral, and anterior surfaces of the torso of patient 114. In other examples, electrodes 182 may be positioned on any one or more of the posterior, lateral, and anterior surfaces of the torso. Electrodes 182 may be electrically connected to an ECG processing unit 184 via a wired connection 186. Some configurations may use a wireless connection to transmit the signals sensed by electrodes 182 to ECG processing unit 184, e.g., as channels of data.

Although in the example of FIG. 1, strap 180 is shown carrying surface electrodes 182, in other examples any of a variety of mechanisms, e.g., tape or adhesives, may be employed to aid in the spacing and placement of electrodes 182. In some examples, strap 180 may include an elastic band, strip of tape, or cloth. In some examples, electrodes 182 may be placed individually on the torso of patient 114.

Electrodes 182 may surround heart 112 of patient 114 and record the electrical signals associated with the depolarization and repolarization of heart 112. Each of electrodes 182 may be used in a unipolar configuration to sense the surface potentials that reflect the cardiac signals. ECG processing unit 184 may also be coupled to a return or indifferent electrode (not shown) which may be used in combination with each of electrodes 182 for unipolar sensing. Another exemplary unipolar LV sensing/pacing vector includes LV cathode-Can (also referred to as housing). In some examples, there may be 12 to 16 electrodes 182 spatially distributed around the torso of patient 114. Other configurations may have more or fewer electrodes 182.

ECG processing unit 184 may record and analyze the surface potential signals, referred to generally herein as "ECG" signals, sensed by electrodes 182. Processing unit 184 may be configured to provide an output to a user indicating electrical conduction of heart 112. The user may make a diagnosis, prescribe CRT, position therapy devices, e.g., leads, or adjust or select treatment parameters based on the indicated electrical conduction.

ECG processing unit 184 may compute activation times directly from sensed surface potential signals. An activation time for each electrode location (of electrodes 182) may be determined as a time period between two events, such as between the QRS complex onset and the minimum derivative during the QRS signal (i.e., the steepest negative slope of the sensed potential signal) at the respective electrode. Values of one or more indices indicative of the temporal and/or spatial distribution of the activation times may be determined as measures or indicators of electrical conduction. These indicators of electrical conduction may be used to evaluate different CRT control parameters and identify an optimal CRT control parameter.

Examples of indices of cardiac electrical conduction that may be calculated from surface potential signals sensed by electrodes 182 include a standard deviation of the determined activation times, a range of activation times, and a percentage of late activations. All or a subset of the surface electrodes (e.g., only electrodes located on the left anterior, left lateral and left posterior regions of the torso) may be used for calculation or computation of the activation times. The range of activation times may be computed as the difference between the maximum and the minimum cardiac activation times determined from all or a subset of electrodes 182. The percentage of late activations estimates the percentage of electrodes 182 whose associated activation times are greater than a certain percentile, for example the 70th percentile, of the QRS complex duration or the determined activation times for electrodes 182. Techniques for determining indices of electrical conduction based on surface activation times are generally disclosed in commonly-assigned pre-grant U.S. Patent Publication No. 2012/0283587 A1 (Ghosh, et al.) hereby incorporated herein by reference in its entirety. Indices of electrical conduction derived from external surface ECG leads are generally described. CRT optimization based on such indices derived from surface ECG leads can be performed at implant or at patient follow-up visits. Techniques disclosed herein, however, enable tuning of pacing timing parameters in an ongoing closed-loop manner to maintain optimal electrical activation of the ventricles in a patient-specific manner.

One or more indices of ventricular conduction based on the surface potential signals sensed by electrodes 182 is used to identify an optimal CRT parameter setting (e.g. AV delay, VV delay, pacing vector, pacing output etc.). A user may program the control parameters into IMD 10 using programmer 170. In some embodiments, ECG processing unit 184 and programmer 170 are in wired or wireless communication or integrated in a common device that enables system 100 to automatically step through multiple CRT parameter settings, record and analyze surface potential signals to obtain one or more ECG-based indices of ventricular conduction, and identify and program an optimal setting for the CRT parameter based on analysis of ventricular electrical activations determined from surface ECG signals.

The strap 180 carrying electrodes 182 is one illustrative embodiment of an apparatus that is useful in recording surface ECG signals from which ventricular activation times can be determined. Other surface cardiac signal recording apparatus may be used for acquiring cardiac signal data from which ventricular activation times can be computed and used in computing ventricular conduction for establishing an optimal setting of one or more CRT control parameters. Other signal recording apparatus and techniques may include 12-lead ECG electrodes, a vest carrying an array of electrodes, and vectorcardiography.

Once an optimal CRT parameter is established based on optimal synchronization of electrical activation signals of the ventricles derived from surface ECG signals, CRT is delivered by IMD 10 using the optimal parameter setting and multiple non-optimal settings increased or decreased, i.e. shifted, from the optimal setting. IMD 10 acquires EGM signals for the optimal setting and multiple non-optimal settings to establish EGM parameter data for differing states of ventricular activation, i.e. different states of optimal electrical conduction of the signal through cardiac tissue (LV, RV, LA, RA) and non-optimal electrical conduction corresponding to different increments or decrements from the optimal setting of the control parameters. This EGM parameter data is stored by IMD 10 and can be used in closed-loop CRT control parameter optimization.

Figure 2:
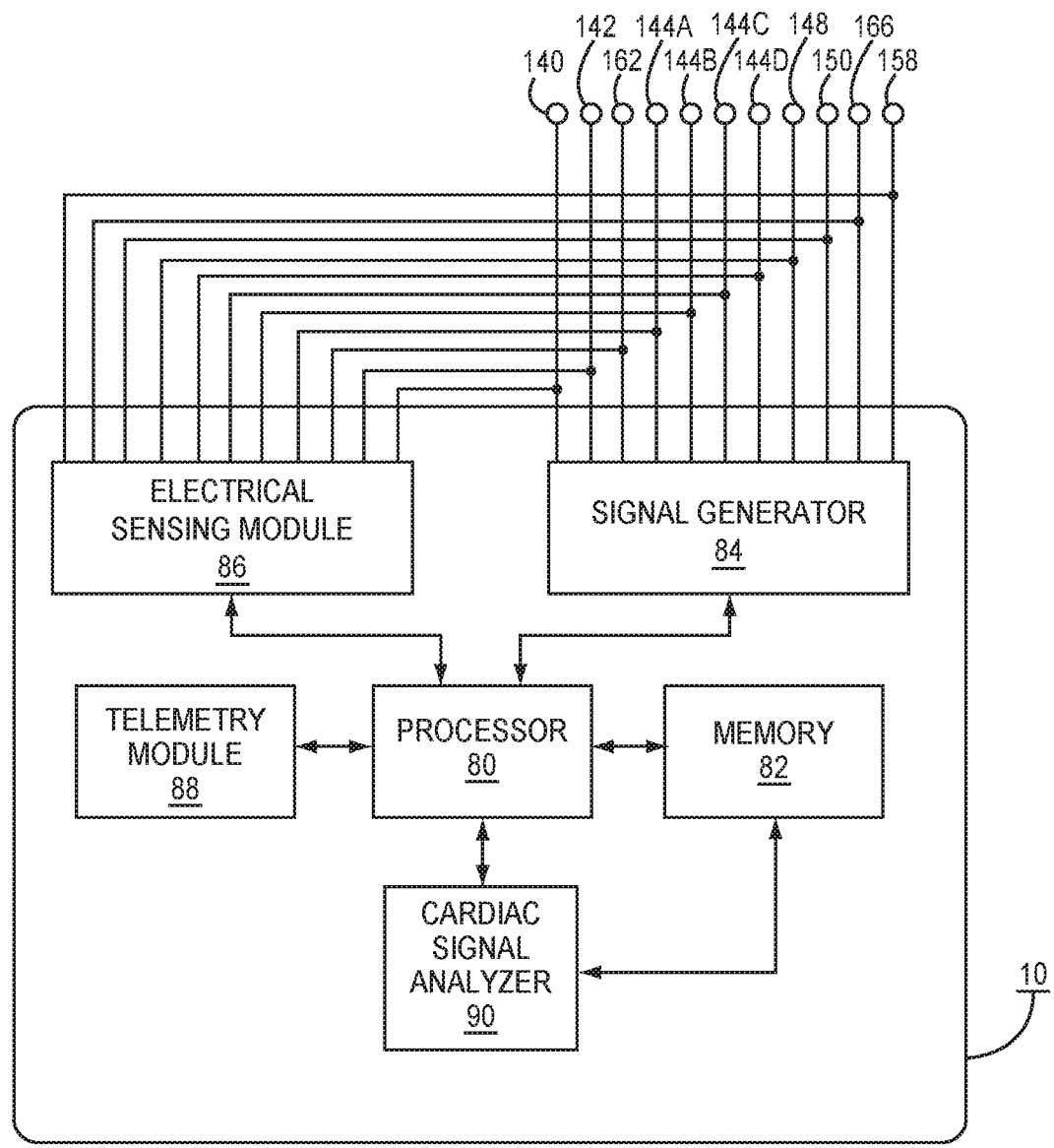
FIG. 2 is a block diagram illustrating one example configuration of the IMD shown in FIG. 1.

FIG. 2 is a block diagram illustrating one example configuration of IMD 10. In the example illustrated by FIG. 2, IMD 10 includes a processor and control unit 80, also referred to herein as "processor" 80, memory 82, signal generator 84, sensing module 86, and telemetry module 88. IMD 10 further includes cardiac signal analyzer 90.

Memory 82 may include computer-readable instructions that, when executed by processor 80, cause IMD 10 and processor 80 to perform various functions attributed throughout this disclosure to IMD 10, processor 80, and cardiac signal analyzer 90. The computer-readable instructions may be encoded within memory 82. Memory 82 may comprise non-transitory, computer-readable storage media including any volatile, non-volatile, magnetic, optical, or electrical media, such as a random-access memory (RAM), read-only memory (ROM), non-volatile RAM (NVRAM), electrically-erasable programmable ROM (EEPROM), flash memory, or any other digital media with the sole exception being a transitory propagating signal.

Processor and control unit 80 may include any one or more of a microprocessor, a controller, a digital signal processor (DSP), an application specific integrated circuit (ASIC), a field-programmable gate array (FPGA), or equivalent discrete or integrated logic circuitry. In some examples, processor 80 may include multiple components, such as any combination of one or more microprocessors, one or more controllers, one or more DSPs, one or more ASICs, or one or more FPGAs, as well as other discrete or integrated logic circuitry. The term "processor" "processor module" or "processing circuitry" may generally refer to any of the foregoing logic circuitry, alone or in combination with other logic circuitry, or any other equivalent circuitry.

The functions attributed to processor 80 herein may be embodied as software, firmware, hardware or any combination thereof. In one example, cardiac signal analyzer 90 may, at least in part, be stored or encoded as instructions in memory 82 that are executed by processor and control unit 80.

Processor and control unit 80 includes a therapy control unit that controls signal generator 84 to deliver electrical stimulation therapy, e.g., cardiac pacing or CRT, to heart 112 according to a selected one or more therapy programs, which may be stored in memory 82. Signal generator 84 is electrically coupled to electrodes 140, 142, 144A-144D (collectively 144), 148, 150, 158, 162, and 166 (all of which are shown in FIG. 1), e.g., via conductors of the respective leads 118, 120, 122, or, in the case of housing electrode 158, via an electrical conductor disposed within housing 160 of IMD 10. Signal generator 84 is configured to generate and deliver electrical stimulation therapy to heart 112 via selected combinations of electrodes 140, 142, 144, 148, 150, 158, 162, and 166. Signal generator 84 delivers cardiac pacing pulses according to AV and/or W delays during CRT. These delays are set based on an analysis of cardiac signals by analyzer 90 as will be described herein.

Signal generator 84 may include a switch module (not shown) and processor and control 80 may use the switch module to select, e.g., via a data/address bus, which of the available electrodes are used to deliver pacing pulses. Processor 80 controls which of electrodes 140, 142, 144A-144D, 148, 150, 158, 162, and 166 is coupled to signal generator 84 for delivering stimulus pulses, e.g., via the switch module. The switch module may include a switch array, switch matrix, multiplexer, or any other type of switching device suitable to selectively couple a signal to selected electrodes.

Sensing module 86 monitors cardiac electrical signals for sensing cardiac electrical events, e.g. P-waves and R-waves, from selected ones of electrodes 140, 142, 144A-144D, 148, 150, 158, 162, or 166 in order to monitor electrical activity of heart 112. Sensing module 86 may also include a switch module to select which of the available electrodes are used to sense the cardiac electrical activity. In some examples, processor 80 selects the electrodes to function as sense electrodes, or the sensing vector, via the switch module within sensing module 86.

Sensing module 86 includes multiple sensing channels, each of which may be selectively coupled to respective combinations of electrodes 140, 142, 144A-144D, 148, 150, 158, 162, or 166 to detect electrical activity of a particular chamber of heart 112. Each sensing channel may comprise an amplifier that outputs an indication to processor 80 in response to sensing of a cardiac depolarization, in the respective chamber of heart 112. In this manner, processor 80 may receive sense event signals corresponding to the occurrence of R-waves and P-waves in the various chambers of heart 112, e.g. ventricular sense events and atrial sense events corresponding to intrinsic depolarization of the respective heart chamber. Sensing module 86 may further include digital signal processing circuitry for providing processor 80 or cardiac signal analyzer 90 with digitized EGM signals. An exemplary cardiac signal morphology waveform analysis method is disclosed in U.S. Pat. No. 8,738,813 published on May 27, 2014 to Ghosh et al., the disclosure of which is incorporated by reference, in its entirety. It will be appreciated that many different morphology waveform analysis methods can be used.

The occurrence of R-waves in the ventricles, e.g. in the RV, may be used in monitoring intrinsic AV conduction time. In particular, prolongation of the AV conduction time or the detection of AV block based on R-wave sensing during no ventricular pacing (or pacing at an extended AV delay that allows intrinsic conduction to take place) is used to control adaptive CRT in some embodiments. When AV conduction is impaired, signal generator 84 is controlled by processor 80 to deliver biventricular pacing, i.e. pacing pulses are delivered in the RV and the LV using a selected AV delay and a selected VV delay. When AV conduction is intact, signal generator 84 is controlled by processor 80 to deliver LV-only pacing at a selected AV delay to optimally improve conduction according to an EGM-based parameter whose relationship to ventricular electrical activation conduction has been previously established.

As described herein, the AV delay may be optimized uniquely for different heart rhythm states such as rhythm states involving atrial sensing, atrial pacing, LV-only pacing, or biventricular pacing. For example, atrioventricular rhythm states may be evaluated: 1) atrial-sensed, biventricular paced, 2) atrial-paced, biventricular paced 3) atrial-sensed, LV-only paced and 4) atrial-pace, LV-only paced. EGM-based conduction data may be established for different rhythm states and used to adjust the pacing control parameters (e.g. AV delay, VV delay, pacing vector, pacing output parameter etc.) according to the sensed EGM-based data and the current atrial sensing or pacing rhythm state and/or LV-only or biventricular pacing state.

Memory 82 stores intervals, counters, or other data used by processor 80 to control the delivery of pacing pulses by signal generator 84. Such data may include intervals and counters used by processor 80 to control the delivery of pacing pulses to one or both of the left and right ventricles for CRT. The intervals and/or counters are, in some examples, used by processor 80 to control the timing of delivery of pacing pulses relative to an intrinsic or paced event in another chamber. Memory 82 stores look-up tables and/or equations established for adjusting CRT control parameters such as AV and VV delays as will be described herein. Equations may be stored in the form of coefficient and intercept values defining a relationship between an EGM-based ventricular conduction parameter and different settings of a control parameter.

Figure 3:
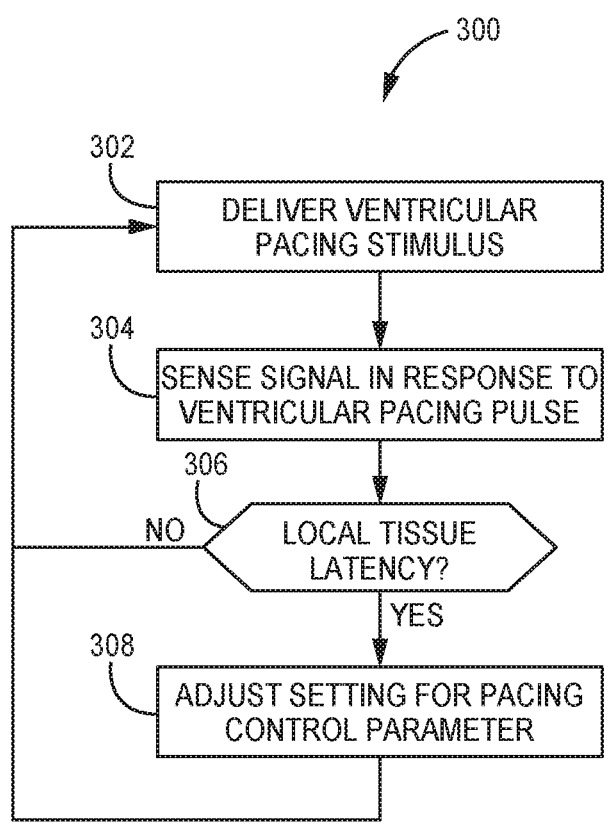
FIG. 3 is a flow chart of a method for adjusting a control parameter such as atrio-ventricular (AV) delay or inter-ventricular (VV) delay in response to determining whether local tissue latency is present.

FIG. 3 is a flow chart of a method 300 by IMD 10 for adjusting one or more pacing control parameters, in a closed loop process, in response to identifying local tissue latency existing in the area of a pacing electrode (e.g. lead etc.). Method 300 begins at block 302 in which a ventricular pacing pulse is generated by signal generator 84 in IMD 10 and delivered to cardiac tissue (e.g. LV, RV) through a pacing electrode at a shortened AV delay. An exemplary shortened AV delay can be equal to or less than 60 ms while the VV may be set to zero. The ventricular pacing pulse can be either a monoventricular pulse (i.e. LV only pacing (FIG. 4), RV only pacing) or a biventricular pulse (FIG. 5). One or more signals (i.e. EGM and/or ECG) are sensed (or acquired by the sensing circuitry of IMD 10) through one or more sensing/pacing vectors in response to the delivered ventricular pacing pulse at block 304. Exemplary sensing/pacing vectors that may be used for sensing an EGM include a LV electrode (e.g. multipolar lead, bipolar LV electrode (i.e. cathode) and a RV coil (i.e. anode) or a unipolar LV cathode-Can (also referred to as housing of IMD 10)).

A monitoring window, is used when acquiring data from an EGM signal. The monitoring window overlays the time period before, during, or following a pacing pulse (or after a blanking interval). For example, the monitoring window along the X-axis can be set from 0 to about 200 ms or less, 190 ms or less, 180 ms or less, 170 ms or less, 160 ms or less, 160 ms or less etc. For the exemplary LV only pacing pulse shown in FIG. 4, the maximum amplitude is about 0.9 my at a time of 150 ms referred to as Tmax_LV and the minimum amplitude is about 1.25 mv at a time of 100 ms referred to as Tmin_LV where both time-intervals Tmin_LV and Tmax_LV are measured from the time when the ventricular pacing stimulus was delivered. For the BV pacing pulse shown in FIG. 5, the maximum amplitude is about 4 millivolts at a time of 80 ms referred to as Tmax_BV and the minimum amplitude is about 3.8 mV at a time of 150 ms referred to as Tmin_BV.

At block 306, a determination is made by processing circuitry in IMD 10 as to whether local tissue latency is detected. The criterion for determining local tissue latency depends on the type of pacing (i.e. monoventricular pacing, biventricular pacing) being performed. If LV only pacing is being delivered to the left ventricle, the criterion used to detect local tissue latency can be whether Tmin exceeds a threshold e.g. Tmin≥100 milliseconds. As applied to the EGM signal sensed in response to LV only pacing (depicted in FIG. 4), Tmin is equal to 100 ms and so local tissue latency is detected. If Tmin is less than 100 ms, local tissue latency is not present. If Tmin is greater than or equal to 100 ms, local tissue latency is present. In yet another embodiment of the criterion, the threshold is lower 100 ms. e.g. Tmin≥80 ms. For example, If LV only pacing is being delivered to the left ventricle, the criterion used to detect local tissue latency can be whether Tmin≥80 milliseconds.

If BV pacing pulses are being delivered, the processor determines whether Tmin>Tmax. If the sensed data indicates Tmin>Tmax, local tissue latency is deemed present. Local tissue latency is not present if Tmin is not greater than Tmax. Additionally, or alternatively, a latency condition exists when |Maxamp−Minampl|/|Tmax−Tmin) is less than a predetermined ratio. Additionally, or alternatively, a latency condition exists and/or |Minamp| is less than a predetermined threshold and effective capture is present.

Table 1, presented below, summarizes the data acquired from EGM signals depicted in FIGS. 4-5.

TABLE 1

Figure 4:
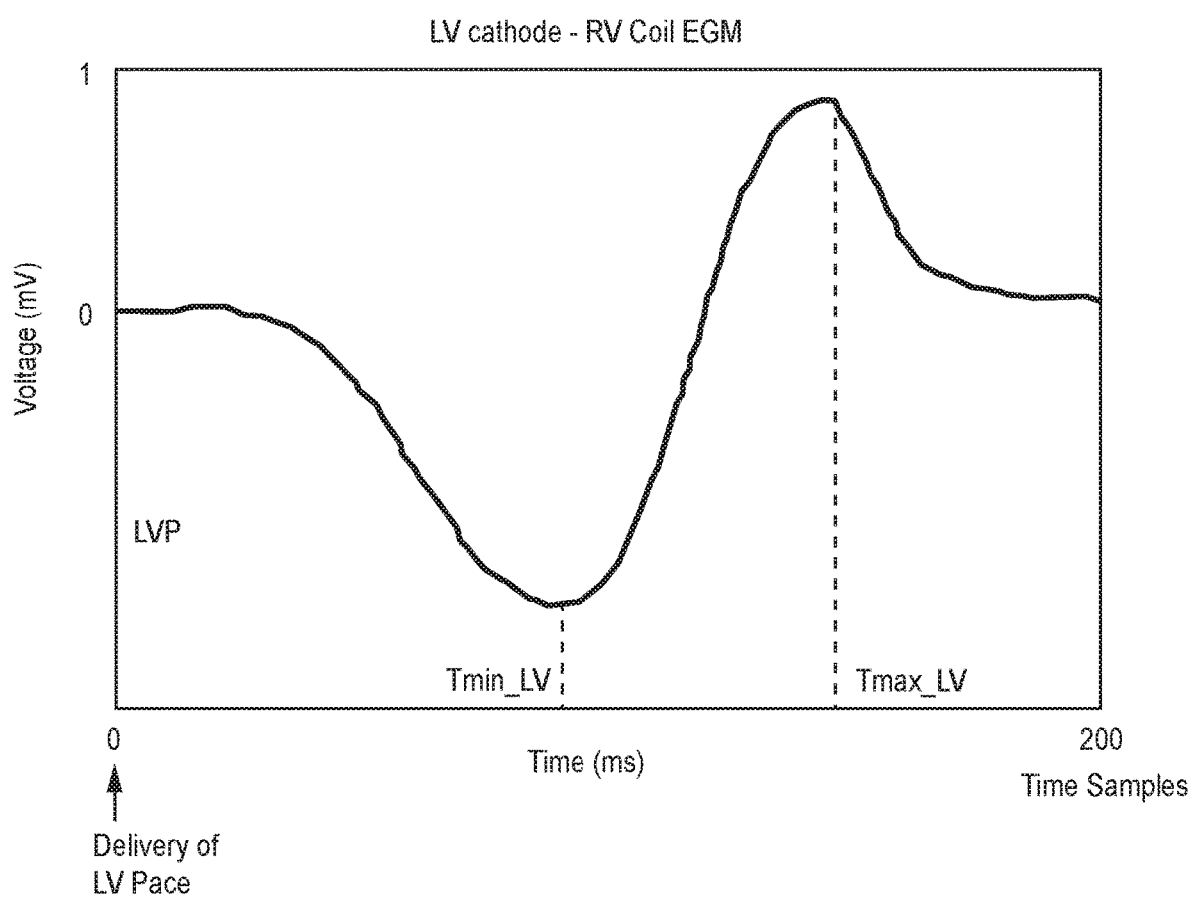
FIG. 4 is an intracardiac electrogram (EGM) signal of a paced beat acquired through left ventricular pacing only of a pacing vector.
Figure 5:
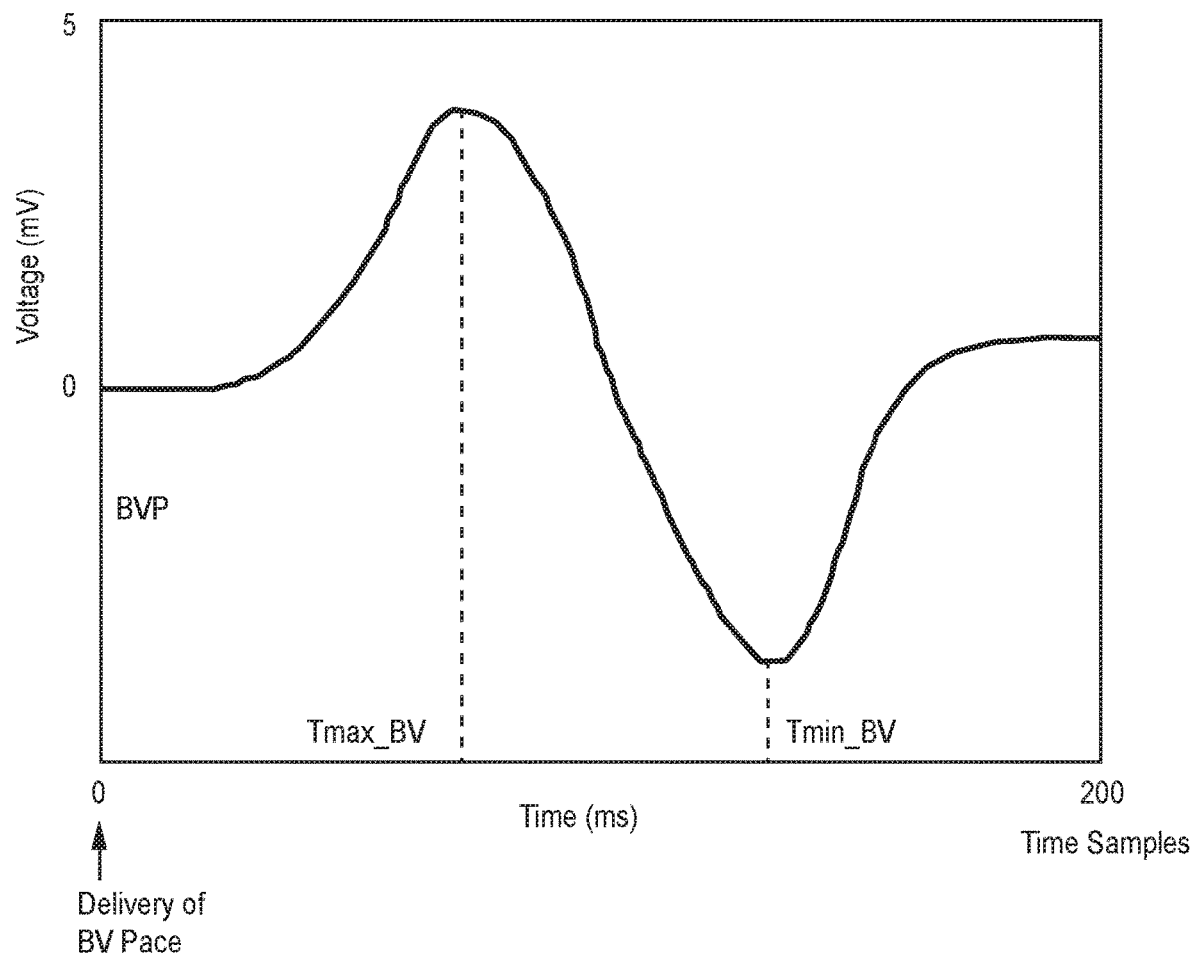
FIG. 5 is an EGM signal of a paced beat acquired through biventricular pacing of a pacing vector.

Summary of local tissue latency examples presented by the EGMs depicted in FIGS. 4-5.

| Parameter or condition | Example 3-FIG. 4 | Example 4-FIG. 5 |
| --- | --- | --- |
| Pacing | Left ventricular pacing only | Biventricular pacing |
| Tmax | 150 ms | 80 ms |
| Tmin | 100 ms | 150 ms |
| Min | 1.25 mV | 4 mV |
| Max | 0.9 mV | 3.8 mV |

TABLE 1-continued

Summary of local tissue latency examples presented by the EGMs depicted in FIGS. 4-5.

| Parameter or condition | Example 3-FIG. 4 | Example 4-FIG. 5 |
|---|---|---|
| Tmin ≥ pre-specified threshold (e.g. 100 ms) for monoventricular pacing | Yes | Not applicable |
| Tmin > Tmax for biventricular pacing | Not applicable | Yes |

At block 308, one or more pacing control parameters is adjusted by processor 80 of IMD 10 if local tissue latency is detected at block 306. For example, one of the timing parameter (e.g. AV delay, VV delay etc.) may be adjusted automatically adjusted by a decrement (e.g. 5 ms, 10 ms, 15 ms, 20 ms, 25 ms, 30 ms, 35 ms, 40 ms) or increment (e.g. 5 ms, 10 ms, 15 ms, 20 ms, 25 ms, 30 ms, 35 ms, 40 ms). One example of adjusting a pacing parameter involved a patient that had tissue latency at VV=0 ms and VV was increased to 40 ms in steps of 20 ms until the tissue latency problem was resolved. The optimal VV delay was set at 40 ms by the processing circuitry of IMD 10. In one or more embodiments, increasing VV delay by 20 ms can be used when determining the optimum VV delay to be used. In another embodiment, the VV delay can be incremented by 10 ms from 0 ms until no tissue latency issue is determined to be present.

Alternatively, the timing parameter may undergo an evaluation period to select an optimal timing parameter during different rhythm conditions or states, e.g. during atrial sensing and/or during atrial pacing (with ventricular pacing occurring in one or both ventricles). In one embodiment, AV delay is set to multiple settings during an atrial pacing rhythm and/or during an atrial sensing rhythm to identify an optimal AV delay during atrial sensing (SAV delay) and during atrial pacing (PAV delay).

Additionally, AV delay may be set to multiple different settings during pacing in one ventricle, RV-only and/or LV-only, and/or during biventricular pacing. During biventricular pacing, multiple settings of VV delay may be tested. For example, once an optimal AV delay is identified using a nominal VV delay, multiple VV delay settings may be applied to determine the optimal VV delay according to an ECG data of ventricular conduction.

In some embodiments, multiple pacing vectors may be available. For example, as shown in FIG. 1, a multi-polar CS lead may include multiple electrodes available for pacing the LV. Accordingly, an optimal AV delay resulting in a minimized ventricular conduction based on surface activation time determinations may be identified for each available pacing vector. When a pacing vector is changed, for example due to a change in lead impedance or other condition, the AV or VV delay may be adjusted to an optimal setting identified for the new pacing vector.

Once an optimal setting is established for a CRT parameter, CRT is delivered at the optimal parameter setting(s). An EGM signal is acquired by sensing module 86 and provided to cardiac signal analyzer 90. Signal analyzer 90 determines a ventricular conduction parameter from the EGM signal at block 308.

An EGM-based index relative to conduction and local tissue latency can be established as a lookup table stored in memory and accessed by the processor in IMD 10. Data is stored for each test setting, along with the difference between the test (non-optimal) setting and the optimal setting for the CRT parameter at block 314. In this way, an EGM-based index is characterized for a known optimal ventricular activation condition, i.e. the optimal CRT parameter setting identified in response to surface ECG analysis, and for multiple non-optimal settings. In other words, a relationship is established between the EGM-based index and multiple parameter settings, including the optimal setting and one or more non-optimal settings different than, i.e. shifted from, the optimal setting.

Knowing the value of the EGM-based index during optimized electrical activation of the ventricles, adjustments to the CRT control parameter may be made to return the EGM-based index toward the value associated with electrical activation with excellent conduction in a closed-loop control method. The optimal control parameter setting, such as AV delay, may change with changes in heart rate, activity or other conditions. This variation in an optimal setting occurs when intrinsic AV conduction timing changes. To maintain optimal ventricular activation under changing conditions, the optimal control parameter setting, like the A-V delay, needs to be adjusted so that the relationship of the timing of a CRT ventricular pacing pulse and the timing of intrinsic ventricular conduction remains consistent. However, to determine the intrinsic AV conduction and its changes directly, ventricular pacing needs to be inhibited temporarily, suspending CRT therapy. Even short disruptions in CRT therapy may be undesirable in some patients. By monitoring the EGM-based index and its changes during CRT pacing, it is possible to detect a need to adjust a timing control parameter without temporary suspension of CRT therapy.

Adjustments to control parameters, such as timing parameters AV delay or VV delay, may be made based on the stored patient-specific relationship and local tissue latency data of the EGM-based index to increments and decrements of the control parameters. In this way, the EGM-based index can be restored to the value associated with optimal electrical activation to elicit a proper response or capture and maintained at this value regardless of heart rate, intrinsic conduction changes or other changing conditions.

To diagnose tissue latency based on the method described above, it is important to ensure that the LV or BV pacing is delivered at adequate energy that results in local tissue capture, as described in U.S. Pat. No. 8,750,998 filed Dec. 6, 2012 and entitled EFFECTIVE CAPTURE TEST and US 2014-0277245 A1 filed Mar. 15, 2013 entitled and MODULATE PACING RATE TO INCREASE THE PERCENTAGE OF EFFECTIVE VENTRICULAR CAPTURE DURING ATRIAL FIBRILLATION, both of which are incorporated by reference in their entirety Latency results in delayed electrical conduction due to diseased substrate near the pacing electrode which is different from inability to capture tissue because of inadequate pacing outputs. The diagnostic method described herein advantageously employs the results from left ventricular capture management (e.g. left ventricular capture management (LVCM) etc.) to determine if the delivered energy is sufficient for local tissue capture. LVCM is a set of computer instructions, executed by the processor, that automatically monitors and, if applicable, adjusts LV output to attempt to secure ventricular capture. LVCM can minimize LV output that is delivered to capture the left ventricle, while enforcing a safety margin of amplitude over the required amplitude for ventricular capture, in order to reduce undesirable effects of electrical stimulation such as phrenic nerve stimulation.

LVCM can also indicate that left ventricular capture cannot be obtained, even with high energy deliveries.

Figure 6:
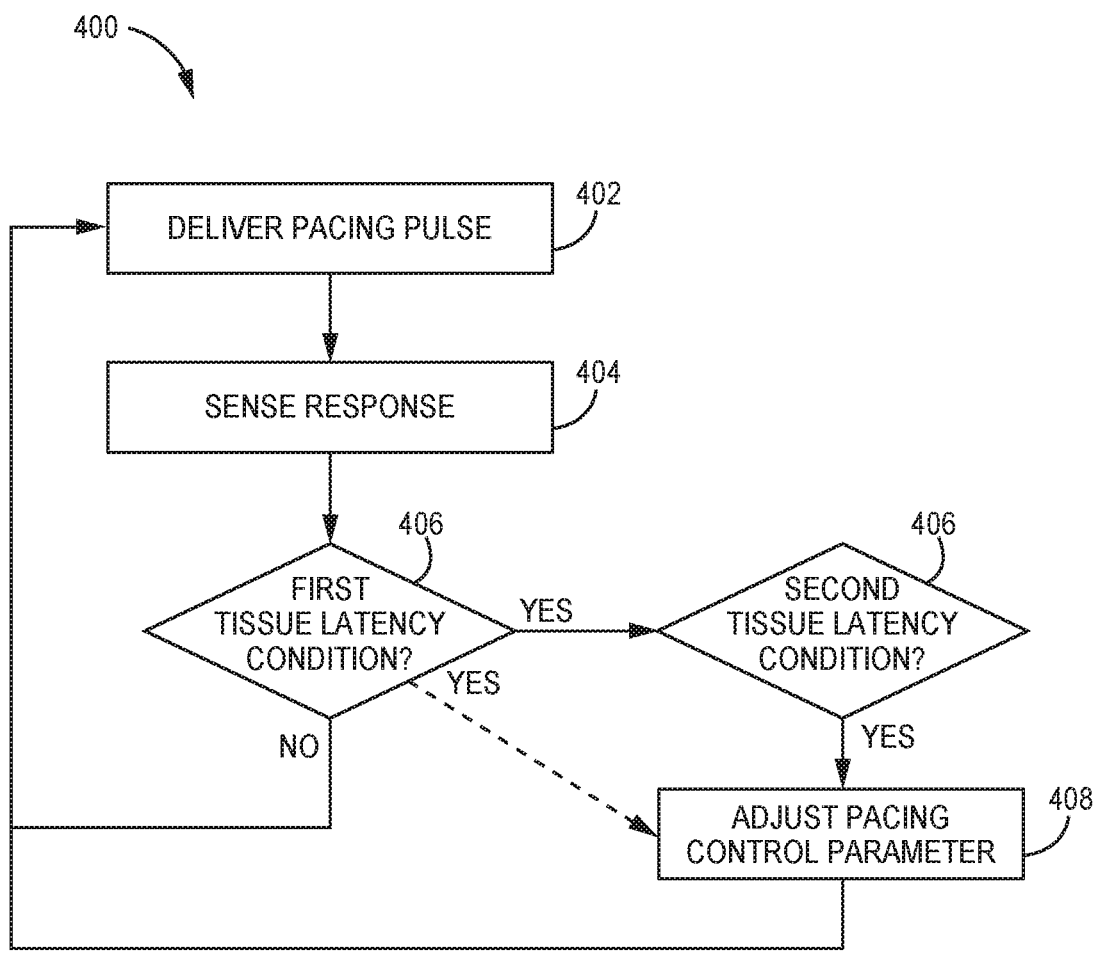
FIG. 6 is a flow chart of another method for adjusting a control parameter such as in response to determining whether local tissue latency is present.

FIG. 6 is a flow chart of a method 400 for IMD 10 automatically adjusting one or more pacing control parameters in response to identifying presence of local tissue latency in an area of a pacing electrode. Implementation of method 400 requires pacing electrode(s) to pace a ventricle (i.e. typically the left ventricle but can also be the right ventricle) through a multipolar lead (FIGS. 7-8) and/or leadless pacing devices. Exemplary multipolar leads includes the ATTAIN PERFORMA™ and an exemplary leadless pacing device includes the MICRA™ device, both of which are commercially available from Medtronic Inc. located in Minneapolis, Minn.

Method 400 begins at block 402 in which left ventricular or biventricular pacing pulses are generated by signal generator 84 of IMD 10 and delivered via a multipolar lead to cardiac tissue (e.g. LV, RV) at a shortened AV delay equal to or less than 60 ms while the VV delay may be set to zero if pacing biventricular with adequate pacing outputs above capture thresholds and overdriving the intrinsic heart rate to ensure ideal conditions of capture. Ideally the latency test with biventricular pacing should run at a simultaneous V-V delay, because with LV pre-excitation or RV pre-excitation the EGM characteristics may be altered due to differential V-V that may affect the sensitivity/specificity of determining latency. One or more signals (i.e. EGM and/or ECG) are sensed (or acquired by sensing module 86) through one or more sensing/pacing vectors in response to the delivered ventricular pacing pulse at block 404. Exemplary sensing/pacing vectors that may be used for sensing an EGM include a bipolar LV electrode (i.e. cathode) and a RV coil (i.e. anode) or a unipolar LV cathode-Can (also referred to as housing of the IMD).

A monitoring window, immediately following a pacing pulse (or after a blanking interval), is used to acquire data from an EGM signal. For example, the monitoring window along the X-axis can be set from 0 to about 200 ms or less, 190 ms or less, 180 ms or less, 170 ms or less, 160 ms or less, 160 ms or less etc. An exemplary LV only pacing pulse is shown in FIG. 4. As shown, the maximum amplitude is about 0.9 my at a time of 150 ms referred to as Tmax_LV and the minimum amplitude is about 1.25 mv at a time of 100 ms referred to as Tmin_LV where both time-intervals Tmin_LV and Tmax_LV are measured from the time when the ventricular pacing stimulus was delivered. The biventricular (BV) signal is shown in FIG. 5. The maximum amplitude is about 4 millivolts (mV) at 80 ms referred to as Tmax_BV and the minimum amplitude is about 3.8 mV at 150 ms referred to as Tmin_BV.

At block 406, a determination is made by processor 80 of IMD 10 as to whether a first local tissue latency condition is detected. The NO path from block 406 returns to processor 80 signaling the generator 84 to generate and deliver pacing pulses to the ventricle at block 402. The YES path from block 406 optionally continues to block 410.

At block 410, a processor 80 determines whether a second local tissue latency condition is detected. The second latency condition is used to confirm that the first tissue latency condition exists.

The first and second latency conditions are selected from either a ratio of the amplitudes over the time data or a Minamp condition. The ratio of (|Maxamp−Minamp|/|Tmax−Tmin|) is less than a predetermined ratio that can range from about 0.05 mV/ms to about 0.15 mV/ms. Preferably, the ratio is 0.1 mV/ms. In one or more other embodiments, tissue latency exists with a pacing electrode (i.e. one of four LV electrode(s) or a leadless pacing device) when Minamp is less than a pre-specified amplitude threshold. In some embodiments, the criteria applied to determine local tissue latency depends on whether the IMD device is pacing using biventricular or LV only therapy. For LV only pacing, the condition for latency detection may comprise evaluation of effective capture during LV only pacing and then checking if Minamp is less than a pre-specified threshold. Latency is determined to be present if conditions of effective capture are satisfied and Minamp is found to be less than the prespecified threshold. For simultaneous biventricular pacing, latency is determined to be present when conditions of effective capture are not satisfied and the ratio of (|Maxamp−Minamp|/|Tmax−Tmin|) is less than a predetermined value. The IMD may use one or both criteria to determine if latency exists for a given LV pacing electrode.

Listed below are exemplary tissue latency ratios and amplitude thresholds that may be employed. Either condition can be used to confirm tissue latency.

TABLE 1

Summary of exemplary tissue latency
ratio and amplitude threshold values.

| Tissue latency ratio (Maxamp-Minamp|/|Tmax-Tmin|) | Amplitude threshold |
|---|---|
| 0.1 mV/ms | 5 mV |
| 0.08 mV/ms | 4.5 mV |
| 0.05 mV/m | 3.5 mV |

Table 2, presented below, summarizes the data acquired from EGM signals depicted in FIGS. 4-5.

TABLE 2

Summary of local tissue latency examples presented
by the EGMs depicted in FIGS. 4-5.

| Parameter or condition | Example 3-FIG. 4 | Example 4-FIG. 5 |
|---|---|---|
| Pacing | Left ventricular pacing only | Biventricular pacing |
| Tmax | 150 ms | 80 ms |
| Tmin | 100 ms | 150 ms |
| Min | 1.25 mV | 4 mV |
| Max | 0.9 mV | 3.8 mV |
| (|Maxamp-Minamp|/ |Tmax-Tmin|) | (0.9-1.25)/(150-100) = 0.007 | (3.8-4)/(80-150) = 0.00285 |

At block 408, one or more pacing control parameters is adjusted if local tissue latency is detected at block 406 or block 410. For example, if latency is determined to be present relative to one LV electrode, but not for other LV electrodes of a quadripolar lead, the device may switch pacing automatically to another LV electrode if currently programmed to pace from the electrode where latency has been determined. In other embodiments, the device may continue to pace from the same electrode but shortening the AV delay if it is pacing LV only or increasing the LV pre-excitation if pacing biventricular. The IMD 10 may conduct an automated test where it adjusts the above timings in steps and tests for latency till the paced EGM parameters no longer satisfy the latency criteria. One of the timing parameter such as AV delay may be adjusted automatically adjusted by a decrement (e.g. 5 ms, 10 ms, 15 ms, 20 ms, 25 ms, 30 ms, 35 ms, 40 ms) or LV-RV delay (with LV ahead of RV) for biventricular pacing may be changed in small increments (e.g. 5 ms, 10 ms, 15 ms, 20 ms, 25 ms, 30 ms, 35 ms, 40 ms). Alternatively, the timing parameter may undergo an evaluation period to select an optimal timing parameter during different rhythm conditions or states, e.g. during atrial sensing and during atrial pacing (with ventricular pacing occurring in one or both ventricles). In one embodiment, AV delay is set to multiple settings during an atrial pacing rhythm and during an atrial sensing rhythm to identify an optimal AV delay during atrial sensing (SAV delay) and during atrial pacing (PAV delay).

Figure 7:
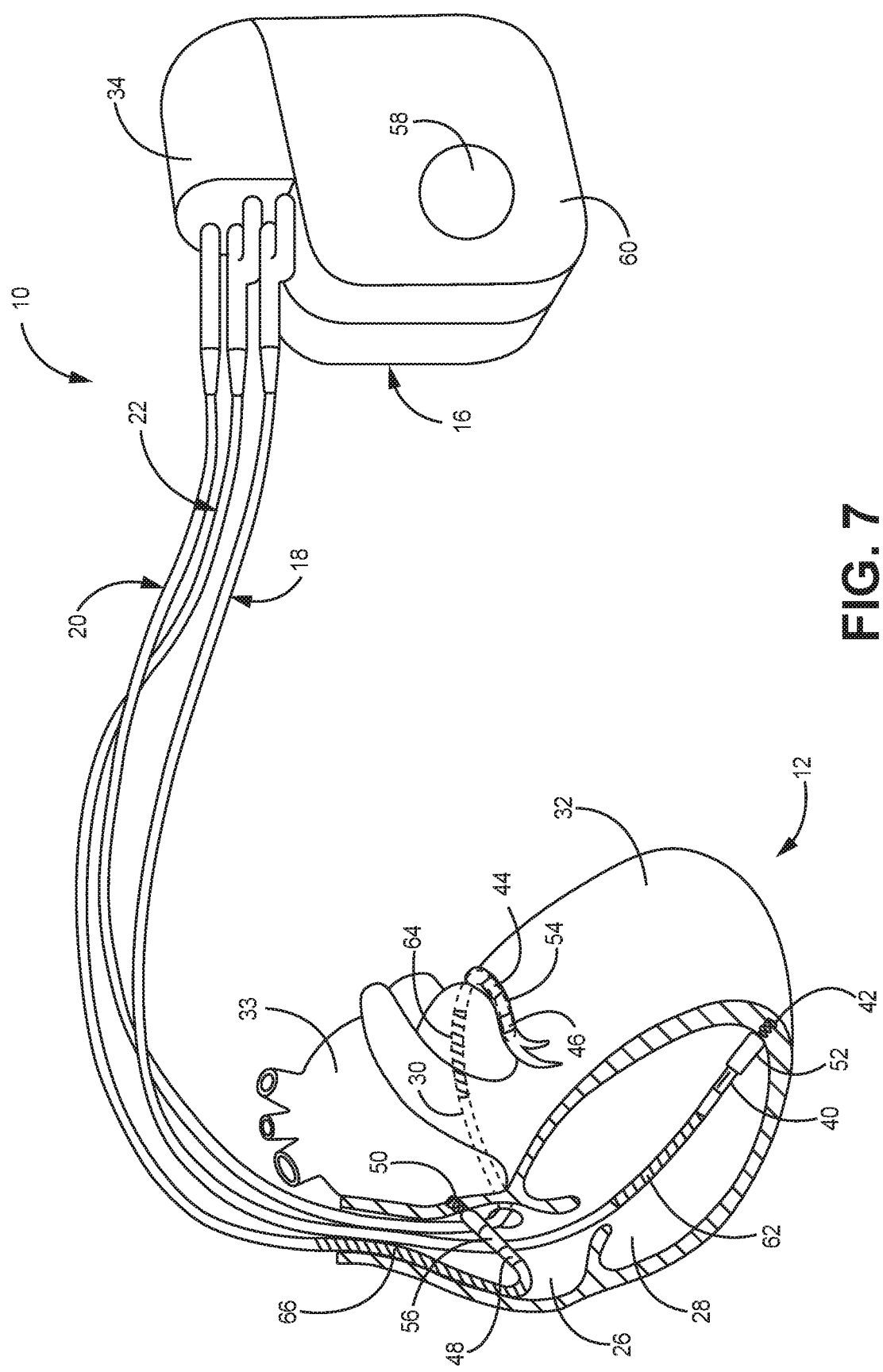
FIG. 7 is a diagram of another exemplary IMD of that can be used to implement the methods described herein.

In some embodiments, multiple pacing vectors may be available. For example, as shown in FIG. 7, a multi-polar CS lead (e.g. ATTAIN PERFORMA™) may include multiple electrodes available for pacing the LV. Accordingly, an optimal AV delay and/or VV delay resulting in a minimized ventricular conduction based on surface activation time determinations may be identified for each available pacing vector. When a pacing vector is changed, for example due to a change in lead impedance or other condition, the AV or W delay may be automatically adjusted by the processing circuitry in IMD 10 to an optimal setting identified for the new pacing vector.

Once an optimal setting is established for a CRT parameter, CRT is delivered at the optimal parameter setting(s). An EGM signal is acquired by sensing module 86 and provided to cardiac signal analyzer 90. Signal analyzer 90 determines a ventricular conduction parameter from the EGM signal.

An EGM-based index relative to conduction and local tissue latency can be established as a lookup table stored in memory and accessed by the processor in IMD 10. Data is stored for each test setting, along with the difference between the test (non-optimal) setting and the optimal setting for the CRT parameter. In this way, an EGM-based index is characterized for a known optimal ventricular activation condition, i.e. the optimal CRT parameter setting identified in response to surface ECG analysis, and for multiple non-optimal settings. In other words, a relationship is established between the EGM-based index and multiple parameter settings, including the optimal setting and one or more non-optimal settings different than, i.e. shifted from, the optimal setting.

To diagnose tissue latency based on the method described above, it may be helpful to ensure that the LV or BV pacing is delivered at adequate energy that results in local tissue capture, as described herein. Latency results in delayed electrical conduction due to diseased substrate near the pacing electrode which is different from inability to capture tissue because of inadequate pacing outputs. The diagnostic method advantageously employs the results from left ventricular capture management (e.g. left ventricular capture management (LVCM) etc.) to determine if the delivered energy is sufficient for local tissue capture. LVCM is a set of computer instructions, executed by the processor, that automatically monitors and, if applicable, adjusts LV output to attempt to secure ventricular capture. LVCM can minimize LV output that is delivered to capture the left ventricle, while enforcing a safety margin of amplitude over the required amplitude for ventricular capture, in order to reduce undesirable effects of electrical stimulation such as phrenic nerve stimulation. LVCM can also indicate that left ventricular capture cannot be obtained, even with high energy deliveries.

Figure 8:
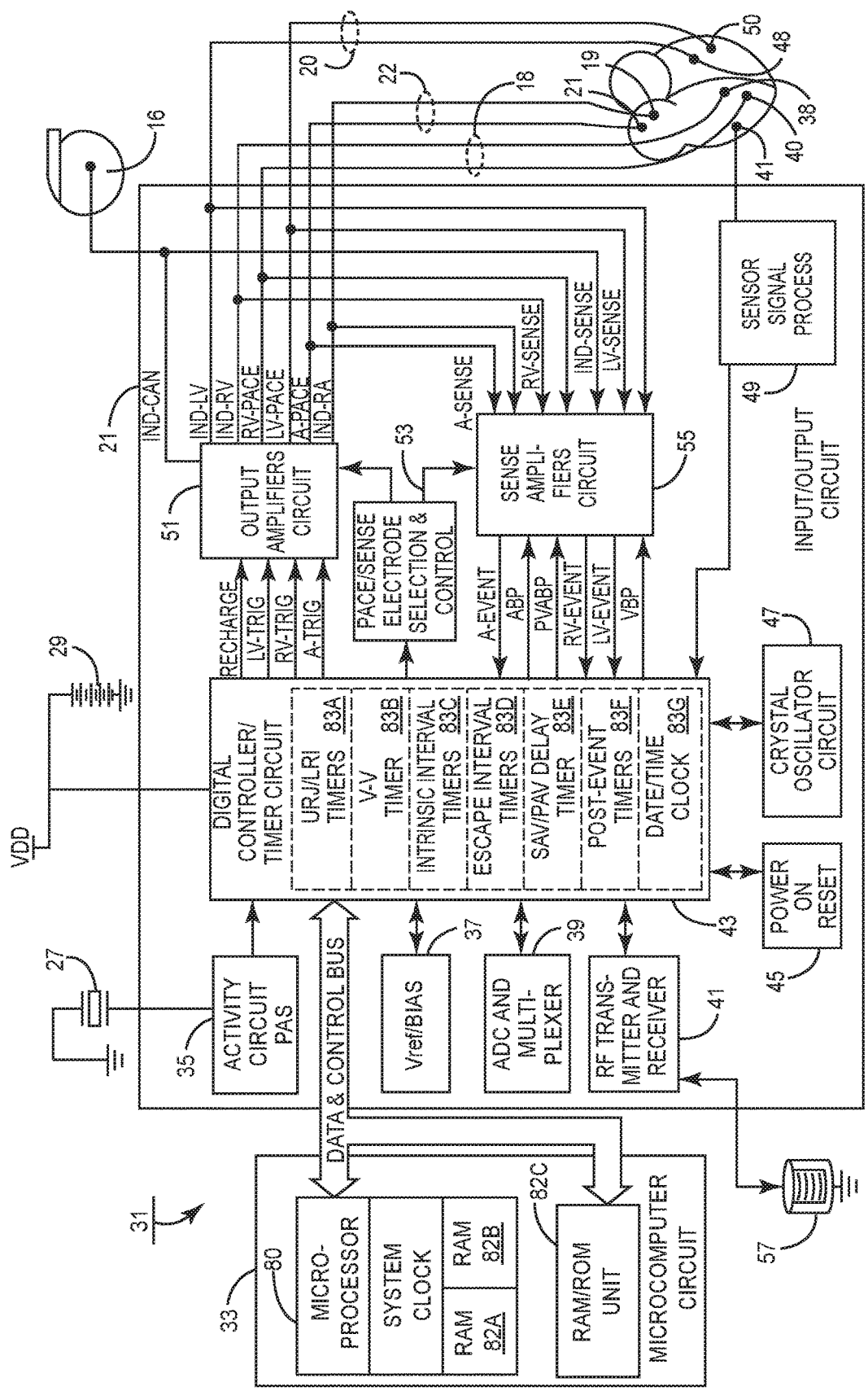
FIG. 8 is yet another block diagram of one embodiment of IMD (e.g. IPG) circuitry and associated leads employed in the system of FIG. 7 for providing three sensing channels and corresponding pacing channels.

FIGS. 7-8 relate to another exemplary therapy system comprising IMD 16 that can be used to implement methods 300 or 400, as described herein. FIG. 7 is a conceptual diagram illustrating the IMD 16 and the leads 18, 20, 22 of therapy system shown in more detail. The leads 18, 20, 22 may be electrically coupled to a therapy delivery module (e.g., for delivery of pacing therapy), a sensing module (e.g., one or more electrodes to sense or monitor electrical activity of the heart 12 for use in determining effectiveness of pacing therapy), and/or any other modules of the IMD 16 via a connector block 34. In some examples, the proximal ends of the leads 18, 20, 22 may include electrical contacts that electrically couple to respective electrical contacts within the connector block 34 of the IMD 16. In addition, in some examples, the leads 18, 20, 22 may be mechanically coupled to the connector block 34 with the aid of set screws, connection pins, or another suitable mechanical coupling mechanism.

Each of the leads 18, 20, 22 includes an elongated insulative lead body, which may carry a number of conductors (e.g., concentric coiled conductors, straight conductors, etc.) separated from one another by insulation (e.g., tubular insulative sheaths). In the illustrated example, bipolar electrodes 40, 42 are located proximate to a distal end of the lead 18. In addition, the bipolar electrodes 44, 46 are located proximate to a distal end of the lead 20 and the bipolar electrodes 48, 50 are located proximate to a distal end of the lead 22.

The electrodes 40, 44, 48 may take the form of ring electrodes, and the electrodes 42, 46, 50 may take the form of extendable helix tip electrodes mounted retractably within the insulative electrode heads 52, 54, 56, respectively. Each of the electrodes 40, 42, 44, 46, 48, 50 may be electrically coupled to a respective one of the conductors (e.g., coiled and/or straight) within the lead body of its associated lead 18, 20, 22, and thereby coupled to respective ones of the electrical contacts on the proximal end of the leads 18, 20, 22.

The electrodes 40, 42, 44, 46, 48, 50 may further be used to sense electrical signals (e.g., morphological waveforms within electrograms (EGM)) attendant to the depolarization and repolarization of the heart 12. The electrical signals are conducted to the IMD 16 via the respective leads 18, 20, 22. In some examples, the IMD 16 may also deliver pacing pulses via the electrodes 40, 42, 44, 46, 48, 50 to cause depolarization of cardiac tissue of the patient's heart 12. In some examples, as illustrated in FIG. 7, the IMD 16 includes one or more housing electrodes, such as housing electrode 58, which may be formed integrally with an outer surface of a housing 60 (e.g., hermetically-sealed housing) of the IMD 16 or otherwise coupled to the housing 60. Any of the electrodes 40, 42, 44, 46, 48, 50 may be used for unipolar sensing or pacing in combination with housing electrode 58. In other words, any of electrodes 40, 42, 44, 46, 48, 50, 58 may be used in combination to form a sensing vector, e.g., a sensing vector that may be used to evaluate and/or analysis the effectiveness of pacing therapy. An example of a configuration sensing and pacing may be seen with respect to U.S. patent application Ser. No. 13/717,896 filed Dec. 18, 2012, and assigned to the assignee of the present invention, the disclosure of which is incorporated by reference in its entirety herein as modified by preferably using a LVtip (i.e. electrode 46)—Rvcoil (i.e. electrode 62) for the pacing vector and the sensing vector, respectively. It is generally understood by those skilled in the art that other electrodes can also be selected as pacing and sensing vectors. Electrode 44 and 64 refer to the third and fourth LV electrodes in the claims.

As described in further detail with reference to FIG. 8, the housing 60 may enclose a therapy delivery module that may include a stimulation generator for generating cardiac pacing pulses and defibrillation or cardioversion shocks, as well as a sensing module for monitoring the patient's heart rhythm. The leads 18, 20, 22 may also include elongated electrodes 62, 64, 66, respectively, which may take the form of a coil. The IMD 16 may deliver defibrillation shocks to the heart 12 via any combination of the elongated electrodes 62, 64, 66 and the housing electrode 58. The electrodes 58, 62, 64, 66 may also be used to deliver cardioversion pulses to the heart 12. Further, the electrodes 62, 64, 66 may be fabricated from any suitable electrically conductive material, such as, but not limited to, platinum, platinum alloy, and/or other materials known to be usable in implantable defibrillation electrodes. Since electrodes 62, 64, 66 are not generally configured to deliver pacing therapy, any of electrodes 62, 64, 66 may be used to sense electrical activity during pacing therapy (e.g., for use in analyzing pacing therapy effectiveness) and may be used in combination with any of electrodes 40, 42, 44, 46, 48, 50, 58. In at least one embodiment, the RV elongated electrode 62 may be used to sense electrical activity of a patient's heart during the delivery of pacing therapy (e.g., in combination with the housing electrode 58 forming a RV elongated, coil, or defibrillation electrode-to-housing electrode vector).

The configuration of the exemplary therapy system illustrated herein is merely one example. In other examples, the therapy system may include epicardial leads and/or patch electrodes instead of or in addition to the transvenous leads 18, 20, 22 illustrated herein. Further, in one or more embodiments, the IMD 16 need not be implanted within the patient 14. For example, the IMD 16 may deliver defibrillation shocks and other therapies to the heart 12 via percutaneous leads that extend through the skin of the patient 14 to a variety of positions within or outside of the heart 12. In one or more embodiments, the therapy system may utilize wireless pacing (e.g., using energy transmission to the intracardiac pacing component(s) via ultrasound, inductive coupling, RF, etc.) and sensing cardiac activation using electrodes on the can/housing and/or on subcutaneous leads.

In other examples of therapy systems that provide electrical stimulation therapy to the heart 12, such therapy systems may include any suitable number of leads coupled to the IMD 16, and each of the leads may extend to any location within or proximate to the heart 12. For example, other examples of therapy systems may include three transvenous leads located as illustrated in FIGS. 1-2. Still further, other therapy systems may include a single lead that extends from the IMD 16 into the right atrium 26 or the right ventricle 28, or two leads that extend into a respective one of the right atrium 26 and the right ventricle 28.

FIG. 8 is yet another embodiment of a functional block diagram for IMD 16. FIG. 8 depicts bipolar RA lead 22, bipolar RV lead 18, and bipolar LV CS lead 20 without the LA CS pace/sense electrodes 28 and 30 coupled with an IPG circuit 31 having programmable modes and parameters of a bi-ventricular DDD/R type known in the pacing art. In turn, the sensor signal processing circuit 49 indirectly couples to the timing circuit 83 and via data and control bus to microcomputer circuitry 33. Optionally, sensor signal process 49 is coupled to another sensor such as an oxygenation sensors, pressure sensors, pH sensors and respiration sensors etc. The IPG circuit 31 is illustrated in a functional block diagram divided generally into a microcomputer circuit 33 and a pacing circuit 83. The pacing circuit includes the digital controller/timer circuit 83, the output amplifiers circuit 51, the sense amplifiers circuit 55, the RF telemetry transceiver 41, the activity sensor circuit 35 as well as a number of other circuits and components described below.

Crystal oscillator circuit 47 provides the basic timing clock for the pacing circuit 320, while battery 29 provides power. Power-on-reset (POR) circuit 45 responds to initial connection of the circuit to the battery for defining an initial operating condition and similarly, resets the operative state of the device in response to detection of a low battery condition. Reference mode circuit 37 generates stable voltage reference and currents for the analog circuits within the pacing circuit 320, while analog to digital converter ADC and multiplexer circuit 39 digitizes analog signals and voltage to provide real time telemetry if a cardiac signals from sense amplifiers 55, for uplink transmission via RF transmitter and receiver circuit 41. Voltage reference and bias circuit 37, ADC and multiplexer 39, power-on-reset circuit 45 and crystal oscillator circuit 47 may correspond to any of those presently used in current marketed implantable cardiac pacemakers.

If the IPG is programmed to a rate responsive mode, the signals output by one or more physiologic sensor are employed as a rate control parameter (RCP) to derive a physiologic escape interval. For example, the escape interval is adjusted proportionally the patient's activity level developed in the patient activity sensor (PAS) circuit 35 in the depicted, exemplary IPG circuit 31. The patient activity sensor 27 is coupled to the IPG housing and may take the form of a piezoelectric crystal transducer as is well known in the art and its output signal is processed and used as the RCP. Sensor 27 generates electrical signals in response to sensed physical activity that are processed by activity circuit 35 and provided to digital controller/timer circuit 83. Activity circuit 35 and associated sensor 27 may correspond to the circuitry disclosed in U.S. Pat. Nos. 5,052,388 and 4,428,378. Similarly, the present invention may be practiced in conjunction with alternate types of sensors such as oxygenation sensors, pressure sensors, pH sensors and respiration sensors, all well known for use in providing rate responsive pacing capabilities. Alternately, QT time may be used as the rate indicating parameter, in which case no extra sensor is required. Similarly, the present invention may also be practiced in non-rate responsive pacemakers.

Data transmission to and from the external programmer is accomplished by means of the telemetry antenna 57 and an associated RF transceiver 41, which serves both to demodulate received downlink telemetry and to transmit uplink telemetry. Uplink telemetry capabilities will typically include the ability to transmit stored digital information, e.g. operating modes and parameters, EGM histograms, and other events, as well as real time EGMs of atrial and/or ventricular electrical activity and Marker Channel pulses indicating the occurrence of sensed and paced depolarizations in the atrium and ventricle, as are well known in the pacing art.

Microcomputer 33 contains a microprocessor 80 and associated system clock and on-processor RAM and ROM chips 82A and 82B, respectively. In addition, microcomputer circuit 33 includes a separate RAM/ROM chip 82C to provide additional memory capacity. Microprocessor 80 normally operates in a reduced power consumption mode and is interrupt driven. Microprocessor 80 is awakened in response to defined interrupt events, which may include A-TRIG, RV-TRIG, LV-TRIG signals generated by timers in digital timer/controller circuit 83 and A-EVENT, RV-EVENT, and LV-EVENT signals generated by sense amplifiers circuit 55, among others. The specific values of the intervals and delays timed out by digital controller/timer circuit 83 are controlled by the microcomputer circuit 33 by means of data and control bus 306 from programmed-in parameter values and operating modes. In addition, if programmed to operate as a rate responsive pacemaker, a timed interrupt, e.g., every cycle or every two seconds, may be provided in order to allow the microprocessor to analyze the activity sensor data and update the basic A-A, V-A, or V-V escape interval, as applicable. In addition, the microprocessor 80 may also serve to define variable, operative AV delay intervals and the energy delivered to each ventricle.

In one embodiment, microprocessor 80 is a custom microprocessor adapted to fetch and execute instructions stored in RAM/ROM unit 82C in a conventional manner. It is contemplated, however, that other implementations may be suitable to practice the present invention. For example, an off-the-shelf, commercially available microprocessor or microcontroller, or custom application-specific, hardwired logic, or state-machine type circuit may perform the functions of microprocessor 80.

Digital controller/timer circuit 83 operates under the general control of the microcomputer 33 to control timing and other functions within the pacing circuit 320 and includes a set of timing and associated logic circuits of which certain ones pertinent to the present invention are depicted. The depicted timing circuits include URI/LRI timers 83A, V-V delay timer 83B, intrinsic interval timers 83C for timing elapsed V-EVENT to V-EVENT intervals or V-EVENT to A-EVENT intervals or the V-V conduction interval, escape interval timers 83D for timing A-A, V-A, and/or V-V pacing escape intervals, an AV delay interval timer 83E for timing the atrial-left ventricular pace (A-LVp) delay (or atrial right ventricular pace (A-RVp delay) from a preceding A-EVENT or A-TRIG, a post-ventricular timer for timing post-ventricular time periods, and a date/time clock 83G.

The AV delay interval timer 83E is loaded with an appropriate delay interval for one ventricular chamber (i.e., either an A-RVp delay or an A-LVp delay as determined using known methods) to time-out starting from a preceding A-PACE or A-EVENT. The interval timer 83E triggers pacing stimulus delivery, and can based on one or more prior cardiac cycles (or from a data set empirically derived for a given patient).

The post-event timers 83F time out the post-ventricular time periods following an RV-EVENT or LV-EVENT or a RV-TRIG or LV-TRIG and post-atrial time periods following an A-EVENT or A-TRIG. The durations of the post-event time periods may also be selected as programmable parameters stored in the microcomputer 33. The post-ventricular time periods include the PVARP, a post-atrial ventricular blanking period (PAVBP), a ventricular blanking period (VBP), a post-ventricular atrial blanking period (PVARP) and a ventricular refractory period (VRP) although other periods can be suitably defined depending, at least in part, on the operative circuitry employed in the pacing engine. The post-atrial time periods include an atrial refractory period (ARP) during which an A-EVENT is ignored for the purpose of resetting any AV delay, and an atrial blanking period (ABP) during which atrial sensing is disabled. It should be noted that the starting of the post-atrial time periods and the AV delays can be commenced substantially simultaneously with the start or end of each A-EVENT or A-TRIG or, in the latter case, upon the end of the A-PACE which may follow the A-TRIG. Similarly, the starting of the post-ventricular time periods and the V-A escape interval can be commenced substantially simultaneously with the start or end of the V-EVENT or V-TRIG or, in the latter case, upon the end of the V-PACE which may follow the V-TRIG. The microprocessor 80 also optionally calculates AV delays, post-ventricular time periods, and post-atrial time periods that vary with the sensor-based escape interval established in response to the RCP(s) and/or with the intrinsic atrial rate.

The output amplifiers circuit 51 contains a RA pace pulse generator (and a LA pace pulse generator if LA pacing is provided), a RV pace pulse generator, and a LV pace pulse generator or corresponding to any of those presently employed in commercially marketed cardiac pacemakers providing atrial and ventricular pacing. In order to trigger generation of an RV-PACE or LV-PACE pulse, digital controller/timer circuit 83 generates the RV-TRIG signal at the time-out of the A-RVp delay (in the case of RV pre-excitation) or the LV-TRIG at the time-out of the A-LVp delay (in the case of LV pre-excitation) provided by AV delay interval timer 83E (or the V-V delay timer 83B). Similarly, digital controller/timer circuit 83 generates an RA-TRIG signal that triggers output of an RA-PACE pulse (or an LA-TRIG signal that triggers output of an LA-PACE pulse, if provided) at the end of the V-A escape interval timed by escape interval timers 83D.

The output amplifiers circuit 51 includes switching circuits for coupling selected pace electrode pairs from among the lead conductors and indifferent electrodes (IND) to the RA pace pulse generator (and LA pace pulse generator if provided), RV pace pulse generator and LV pace pulse generator. Indifferent electrode means any electrode that has no interaction with a designated element. For example, there is no interaction between the atrial electrodes and the LV electrode (i.e. no pacing, sensing, or even sub-threshold measurements) since that pathway has no value. If a RV electrode can interact with the LV electrode, then the RV electrode cannot be defined as being indifferent unless specifically defined as isolated from the LV electrode.

Pace/sense electrode pair selection and control circuit 53 selects lead conductors and associated pace electrode pairs to be coupled with the atrial and ventricular output amplifiers within output amplifiers circuit 51 for accomplishing RA, LA, RV and LV pacing.

The sense amplifiers circuit 55 contains sense amplifiers corresponding to any of those presently employed in contemporary cardiac pacemakers for atrial and ventricular pacing and sensing. As noted in the above-referenced, commonly assigned, '324 patent, it has been common in the prior art to use very high impedance P-wave and R-wave sense amplifiers to amplify the voltage difference signal which is generated across the sense electrode pairs by the passage of cardiac depolarization wavefronts. The high impedance sense amplifiers use high gain to amplify the low amplitude signals and rely on pass band filters, time domain filtering and amplitude threshold comparison to discriminate a P-wave or R-wave from background electrical noise. Digital controller/timer circuit 83 controls sensitivity settings of the atrial and ventricular sense amplifiers 55.

The sense amplifiers are typically uncoupled from the sense electrodes during the blanking periods before, during, and after delivery of a pace pulse to any of the pace electrodes of the pacing system to avoid saturation of the sense amplifiers. The sense amplifiers circuit 55 includes blanking circuits for uncoupling the selected pairs of the lead conductors and the IND_CAN electrode on lead 20 from the inputs of the RA sense amplifier (and LA sense amplifier if provided), RV sense amplifier and LV sense amplifier during the ABP, PVABP and VBP. The sense amplifiers circuit 55 also includes switching circuits for coupling selected sense electrode lead conductors and the IND_CAN electrode on lead 20 to the RA sense amplifier (and LA sense amplifier if provided), RV sense amplifier and LV sense amplifier. Again, sense electrode selection and control circuit 53 selects conductors and associated sense electrode pairs to be coupled with the atrial and ventricular sense amplifiers within the output amplifiers circuit 51 and sense amplifiers circuit 55 for accomplishing RA, LA, RV and LV sensing along desired unipolar and bipolar sensing vectors.

Right atrial depolarizations or P-waves in the RA-SENSE signal that are sensed by the RA sense amplifier result in a RA-EVENT signal that is communicated to the digital controller/timer circuit 83. Similarly, left atrial depolarizations or P-waves in the LA-SENSE signal that are sensed by the LA sense amplifier, if provided, result in a LA-EVENT signal that is communicated to the digital controller/timer circuit 83. Ventricular depolarizations or R-waves in the RV-SENSE signal are sensed by a ventricular sense amplifier result in an RV-EVENT signal that is communicated to the digital controller/timer circuit 83. Similarly, ventricular depolarizations or R-waves in the LV-SENSE signal are sensed by a ventricular sense amplifier result in an LV-EVENT signal that is communicated to the digital controller/timer circuit 83. The RV-EVENT, LV-EVENT, and RA-EVENT, LA-SENSE signals may be refractory or non-refractory, and can inadvertently be triggered by electrical noise signals or aberrantly conducted depolarization waves rather than true R-waves or P-waves.

A feature-based classification may enable beat-to-beat rhythm classification in a device (e.g., IMD 16) employing cardiac pacing (e.g., CRT pacing such as left ventricular fusion pacing, biventricular pacing (BiV), multisite LV pacing etc.) and may add value to the device by providing useful diagnostic indices to a physician. The computational price involved in such feature-based beat-to-beat classifications may be minimal and may be implemented within the architecture of devices such as the IMD 16 described herein. For example, the exemplary methods described herein may combine algebraic operations and comparisons and/or may require a single normalization per beat compared to multiple intensive mathematical operations and normalizations that are often required for detailed template matching algorithms.

ILLUSTRATIVE EMBODIMENTS

Embodiment 1

A cardiac pacemaker, comprising:
(a) a pulse generator configured to deliver a pacing pulse to a patient's ventricle at an atrioventricular (AV) delay following a preceding atrial event;
(b) a sensing circuitry configured to sense a signal from the patient's ventricle following delivery of a said pacing pulse;
(c) a processing circuitry coupled to the pulse generator and the sensing circuitry and configured to control the pulse generator, the processing circuitry further configured to:
  (1) acquire from the sensed signal a set of features comprising minimum amplitude, a minimum time (Tmin) associated with the minimum amplitude (Minamp), maximum amplitude, a maximum time (Tmax) associated with the maximum amplitude (Maxamp);
  (2) determine whether the ventricular pacing pulse effectively captures the patient's ventricle using the set of features;
  (3) determine whether one or more tissue latency conditions are present, the latency conditions comprising:
    a) |Maxamp−Minamp|/|Tmax−Tmin) is less than a predetermined ratio; and
    b.) |Minamp| is less than a predetermined threshold and effective capture is present;
  (4) adjust one or more pacing pulse parameters, in response to determining that tissue latency is present, the pacing pulse parameters being one or more of AV delay, inter-ventricular (VV) delay, pacing vector, and pacing output; and
  (5) control the pulse generator to thereafter deliver pacing pulses having the adjusted one or more pacing pulse parameters.

Embodiment 2

A cardiac pacemaker according to embodiment 1 wherein the predetermined ratio is about 0.1 mV/ms.

Embodiment 3

A cardiac pacemaker according to embodiments 1 or 2 wherein a multipolar lead is employed to deliver pacing stimulus to a left ventricle.

Embodiment 4

A cardiac pacemaker according to embodiments 1 through 3 wherein a lead is employed to deliver pacing stimulus to a right ventricle.

Embodiment 5

A cardiac pacemaker according to embodiment 4 wherein the multipolar lead comprises four or more electrodes.

Embodiment 6

A cardiac pacemaker according to embodiments 3 through 5 wherein the multipolar lead comprises four or more left ventricular (LV) electrodes, each electrode is paced at a short AV delay less (<) than or equal 60 milliseconds (ms) with sufficient energy for LV capture while non-paced LV electrodes can be used for sensing a response to the delivered pace.

Embodiment 7

A cardiac pacemaker according to embodiments 4 through 6 wherein the processing circuitry is further configured to determine presence of tissue latency in response to delivery of pacing stimulus, wherein the Minamp is less than a prespecified amplitude threshold.

Embodiment 8

A cardiac pacemaker according to embodiments 4 through 7 wherein the processing circuitry further configured to determine presence of tissue latency in response to delivery of pacing stimulus, wherein the ratio of (|Maxamp−Minamp|/|Tmax−Tmin|) is less than a predetermined ratio.

Embodiment 9

A cardiac pacemaker according to embodiment 8 further comprising:
a graphical user interface for displaying presence of tissue latency at a LV electrode in response to delivery of pacing stimulus.

Embodiment 10

A cardiac pacemaker of embodiments 1 through 9 wherein a processing circuitry is configured for determining local tissue latency exists in response to determining that the (|Maxamp−Minamp|/|Tmax−Tmin|) is less than a predetermined ratio.

Embodiment 11

A cardiac pacemaker of embodiments 3 through 10 wherein the AV delay is shortened to a short AV delay in response to determining that the (|Maxamp−Minamp|/|Tmax−Tmin|) is less than a predetermined ratio.

Embodiment 12

A cardiac pacemaker of embodiments 3 through 11 wherein the AV delay is shortened to be less than or equal to 80 ms.

Embodiment 13

A cardiac pacemaker of embodiments 6 through 12 wherein the AV delay decreased by a prespecified level being one of 5 ms, 10 ms, 15 ms, 20 ms, 25 ms, 30 ms, 35 ms, and 50 ms.

Embodiment 14

A cardiac pacemaker of embodiments 1 through 13, wherein acquiring the signal comprises selecting a sensing vector comprising a left ventricular electrode and a right ventricular coil electrode.

Embodiment 15

A cardiac pacemaker of embodiments 1 through 14, wherein the signal generator is configured to deliver a biventricular pacing at the short AV delay.

Embodiment 16

A cardiac pacemaker of embodiments 1 through 15, wherein the processing circuitry further configured to adjust the VV delay so that the left ventricular pacing stimulus is delivered ahead of the right ventricular pacing stimulus.

Embodiment 17

A cardiac pacemaker of embodiments 1 through 16, wherein the left ventricular pacing stimulus is delivered ahead of the right ventricular pacing stimulus in about 5 ms or more, 10 ms or more, 15 ms or more, 20 ms or more, 25 ms or more, 30 ms or more, 35 ms or more, and 40 ms or more.

Embodiment 18

A non-transitory, computer-readable storage medium comprising instructions that, when executed, cause a processor included in a medical device system to:
(a) deliver a left ventricular pacing stimulus at a short atrioventricular (AV) delay equal to or less than 60 ms;
(b) sense a signal in response to the ventricular pacing stimulus;
(c) determine from the signal a minimum time (Tmin) associated with the minimum amplitude (Minamp) determining from the signal a minimum amplitude, a minimum time (Tmin) associated with the minimum amplitude, maximum amplitude, a maximum time (Tmax) associated with the maximum amplitude (Maxamp);
(d) determine whether (|Maxamp−Minamp|/|Tmax−Tmin|) is less than a predetermined ratio; and
(e) determine whether to adjust one or more control pacing parameters, in response to determining whether (|Maxamp−Minamp|/|Tmax−Tmin|) is less than the predetermined ratio, wherein the control pacing parameters being one of AV delay, inter-ventricular (VV) delay, pacing vector, and pacing output.

Embodiment 19

A method of using an implantable pacemaker, comprising:
(a) delivering, with the pacemaker, a pacing pulse to a patient's ventricle at an atrioventricular (AV) delay following a preceding atrial event;
(b) sensing, with the pacemaker, a signal from the patient's ventricle following delivery of a said pacing pulse;
(c) acquiring from the sensed signal, with the pacemaker, a set of features comprising minimum amplitude, a minimum time (Tmin) associated with the minimum amplitude (Minamp), maximum amplitude, a maximum time (Tmax) associated with the maximum amplitude (Maxamp);
(d) determining, with the pacemaker, whether the ventricular pacing pulse effectively captures the patient's ventricle using the set of features;
(e) determining, with the pacemaker, whether one or more tissue latency conditions are present, the latency conditions comprising:
  a) |Maxamp−Minamp|/|Tmax−Tmin) is less than a predetermined ratio; and
  b.) |Minamp| is less than a predetermined threshold and effective capture is present;
(f) adjusting, with the pacemaker, one or more pacing pulse parameters, in response to determining that tissue latency is present, the pacing pulse parameters being one or more of AV delay, inter-ventricular (W) delay, pacing vector, and pacing output; and
(g) controlling, with the pacemaker, the pulse generator to thereafter deliver pacing pulses having the adjusted one or more pacing pulse parameters.

Embodiment 20

A medical device system comprising means to perform the method of embodiment 19.

Embodiment 21

A computer-readable storage medium comprising instructions that, when executed by processing circuitry of a medical device system, cause the processing circuitry to perform the method of embodiment 19.

Embodiment 22

A method of any embodiments of 1 through 19.

Thus, various embodiments of an IMD system and method for closed or open loop adjustment of a CRT control parameter (e.g. AV delay, VV delay etc.) have been described. However, one of ordinary skill in the art will appreciate that various modifications may be made to the described embodiments without departing from the scope of the claims. These and other examples are within the scope of the following claims.

The invention claimed is:

1. A cardiac pacemaker, comprising:
   (a) a pulse generator configured to deliver a pacing pulse to a patient's ventricle at an atrioventricular (AV) delay following a preceding atrial event;
   (b) a sensing circuitry configured to sense a signal from the patient's ventricle following delivery of a said pacing pulse;
   (c) a processing circuitry coupled to the pulse generator and the sensing circuitry and configured to control the pulse generator, the processing circuitry further configured to:
      (1) acquire from the sensed signal a set of features comprising minimum amplitude, a minimum time (Tmin) associated with the minimum amplitude (Minamp), maximum amplitude, a maximum time (Tmax) associated with the maximum amplitude (Maxamp);
      (2) determine whether the ventricular pacing pulse effectively captures the patient's ventricle using the set of features;
      (3) determine whether one or more tissue latency conditions are present, the latency conditions comprising:
         a) |Maxamp−Minamp|/|Tmax−Tmin) is less than a predetermined ratio; and
         b.) |Minamp| is less than a predetermined threshold and effective capture is present;
      (4) adjust one or more pacing pulse parameters, in response to determining that tissue latency is present, the pacing pulse parameters being one or more of AV delay, inter-ventricular (VV) delay, pacing vector, and pacing output; and
      (5) control the pulse generator to thereafter deliver pacing pulses having the adjusted one or more pacing pulse parameters.

2. A cardiac pacemaker according to claim 1 wherein the predetermined ratio is about 0.1 mV/ms.

3. A cardiac pacemaker according to claim 1 wherein a multipolar lead is employed to deliver pacing stimulus to a left ventricle.

4. A cardiac pacemaker according to claim 3 wherein a lead is employed to deliver pacing stimulus to a right ventricle.

5. A cardiac pacemaker according to claim 4 wherein the multipolar lead comprises four or more electrodes.

6. A cardiac pacemaker according to claim 4 wherein the processing circuitry is further configured to determine presence of tissue latency in response to delivery of pacing stimulus, wherein the Minamp is less than a prespecified amplitude threshold.

7. A cardiac pacemaker according to claim 4 wherein the processing circuitry further configured to determine presence of tissue latency in response to delivery of pacing stimulus, wherein the ratio of (|Maxamp−Minamp|/|Tmax−Tmin|) is less than a predetermined ratio.

8. A cardiac pacemaker according to claim 7 further comprising:
   a graphical user interface for displaying presence of tissue latency at a LV electrode in response to delivery of pacing stimulus.

9. A cardiac pacemaker according to claim 3 wherein the multipolar lead comprises four or more left ventricular (LV) electrodes, each electrode is paced at a short AV delay less (<) than or equal 60 milliseconds (ms) with sufficient energy for LV capture while non-paced LV electrodes can be used for sensing a response to the delivered pace.

10. A cardiac pacemaker of claim 9 wherein the AV delay decreased by a prespecified level being one of 5 ms, 10 ms, 15 ms, 20 ms, 25 ms, 30 ms, 35 ms, and 50 ms.

11. A cardiac pacemaker of claim 3 wherein the AV delay is shortened to a short AV delay in response to determining that the
(|Maxamp−Minamp|/|Tmax−Tmin|) is less than a predetermined ratio.

12. A cardiac pacemaker of claim 3 wherein the AV delay is shortened to be less than or equal to 80 ms.

13. A cardiac pacemaker of claim 1 wherein a processing circuitry is configured for determining local tissue latency exists in response to determining that the (|Maxamp−Minamp|/|Tmax−Tmin|) is less than a predetermined ratio.

14. A cardiac pacemaker of claim 1, wherein acquiring the signal comprises selecting a sensing vector comprising a left ventricular electrode and a right ventricular coil electrode.

15. A cardiac pacemaker of claim 1, wherein the signal generator is configured to deliver a biventricular pacing at the short AV delay.

16. A cardiac pacemaker of claim 1, wherein the processing circuitry further configured to adjust the VV delay so that the left ventricular pacing stimulus is delivered ahead of the right ventricular pacing stimulus.

17. A cardiac pacemaker of claim 1, wherein the left ventricular pacing stimulus is delivered ahead of the right ventricular pacing stimulus in about 5 ms or more, 10 ms or more, 15 ms or more, 20 ms or more, 25 ms or more, 30 ms or more, 35 ms or more, and 40 ms or more.

18. A non-transitory, computer-readable storage medium comprising instructions that, when executed, cause a processor included in a medical device system to:
   (a) deliver a left ventricular pacing stimulus at a short atrioventricular (AV) delay equal to or less than 60 ms;
   (b) sense a signal in response to the ventricular pacing stimulus;
   (c) determine from the signal a minimum time (Tmin) associated with the minimum amplitude (Minamp) determining from the signal a minimum amplitude, a minimum time (Tmin) associated with the minimum amplitude, maximum amplitude, a maximum time (Tmax) associated with the maximum amplitude (Maxamp);
   (d) determine whether (|Maxamp−Minamp|/|Tmax−Tmin|) is less than a predetermined ratio; and
   (e) determine whether to adjust one or more control pacing parameters, in response to determining whether (|Maxamp−Minamp|/|Tmax−Tmin|) is less than the predetermined ratio, wherein the control pacing parameters being one of AV delay, inter-ventricular (VV) delay, pacing vector, and pacing output.

19. A method of using an implantable pacemaker, comprising:
   (a) delivering, with the pacemaker, a pacing pulse to a patient's ventricle at an atrioventricular (AV) delay following a preceding atrial event;
   (b) sensing, with the pacemaker, a signal from the patient's ventricle following delivery of a said pacing pulse;
   (c) acquiring from the sensed signal, with the pacemaker, a set of features comprising minimum amplitude, a minimum time (Tmin) associated with the minimum amplitude (Minamp), maximum amplitude, a maximum time (Tmax) associated with the maximum amplitude (Maxamp);

(d) determining, with the pacemaker, whether the ventricular pacing pulse effectively captures the patient's ventricle using the set of features;

(e) determining, with the pacemaker, whether one or more tissue latency conditions are present, the latency conditions comprising:
  a) |Maxamp−Minamp|/|Tmax−Tmin) is less than a predetermined ratio; and
  b.) |Minamp| is less than a predetermined threshold and effective capture is present;

(f) adjusting, with the pacemaker, one or more pacing pulse parameters, in response to determining that tissue latency is present, the pacing pulse parameters being one or more of AV delay, inter-ventricular (VV) delay, pacing vector, and pacing output; and (g) controlling, with the pacemaker, the pulse generator to thereafter deliver pacing pulses having the adjusted one or more pacing pulse parameters.

20. A medical device system configured to perform the method of claim 19.

21. A computer-readable storage medium comprising instructions that, when executed by processing circuitry of a medical device system, cause the processing circuitry to perform the method of claim 19.

\* \* \* \* \*